US009648871B2

(12) United States Patent
Li et al.

(10) Patent No.: US 9,648,871 B2
(45) Date of Patent: *May 16, 2017

(54) METHODS TO PRODUCE POLYMER NANOPARTICLES AND FORMULATIONS OF ACTIVE INGREDIENTS

(71) Applicant: Vive Crop Protection Inc., Toronto (CA)

(72) Inventors: Fugang Li, Richmond Hill (CA); Hung Hoang Pham, Brampton (CA); Darren J. Anderson, Toronto (CA)

(73) Assignee: Vive Crop Protection Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,805

(22) Filed: May 16, 2016

(65) Prior Publication Data
US 2016/0255831 A1 Sep. 8, 2016

Related U.S. Application Data

(63) Continuation of application No. 14/292,667, filed on May 30, 2014, now Pat. No. 9,363,994, which is a continuation of application No. 13/741,673, filed on Jan. 15, 2013, now Pat. No. 8,741,808, which is a continuation of application No. 13/299,214, filed on Nov. 17, 2011, now abandoned, which is a continuation of application No. 12/775,049, filed on May 6, 2010, now Pat. No. 8,084,397, which is a continuation of application No. PCT/IB2009/006947, filed on Sep. 25, 2009.

(60) Provisional application No. 61/158,483, filed on Mar. 9, 2009, provisional application No. 61/100,068, filed on Sep. 25, 2008.

(51) Int. Cl.
| | |
|---|---|
| *A01N 25/10* | (2006.01) |
| *A01N 43/40* | (2006.01) |
| *A01N 51/00* | (2006.01) |
| *A01N 25/28* | (2006.01) |
| *A01N 25/34* | (2006.01) |
| *B82Y 30/00* | (2011.01) |
| *C08J 3/14* | (2006.01) |
| *C08K 5/00* | (2006.01) |
| *C08J 3/24* | (2006.01) |
| *C08J 3/28* | (2006.01) |

(52) U.S. Cl.
CPC ............ *A01N 25/10* (2013.01); *A01N 25/28* (2013.01); *A01N 25/34* (2013.01); *A01N 43/40* (2013.01); *A01N 51/00* (2013.01); *B82Y 30/00* (2013.01); *C08J 3/14* (2013.01); *C08J 3/24* (2013.01); *C08J 3/28* (2013.01); *C08K 5/0058* (2013.01); *C08J 2333/02* (2013.01); *C08J 2339/02* (2013.01); *C08K 2201/011* (2013.01); *Y10T 428/2982* (2015.01)

(58) Field of Classification Search
None
See application file for complete search history.

(56) References Cited

U.S. PATENT DOCUMENTS

| | | |
|---|---|---|
| 6,197,394 B1 | 3/2001 | Mild et al. |
| 6,262,152 B1 | 7/2001 | Fryd et al. |
| 6,383,500 B1 | 5/2002 | Wooley et al. |
| 6,572,672 B2 | 6/2003 | Yadav et al. |
| 6,638,994 B2 | 10/2003 | Crooks et al. |
| 7,063,895 B2 | 6/2006 | Rodrigues et al. |
| 7,070,795 B1 | 7/2006 | Botts et al. |
| 7,101,575 B2 | 9/2006 | Donath et al. |
| 7,501,180 B2 | 3/2009 | Anderson et al. |
| 7,534,490 B1 | 5/2009 | Goh et al. |
| 7,666,506 B2 | 2/2010 | Rieger et al. |
| 8,084,397 B2 | 12/2011 | Li et al. |
| 8,741,808 B2 | 6/2014 | Li et al. |
| 9,363,994 B2 | 6/2016 | Li et al. |
| 2004/0091546 A1 | 5/2004 | Johnson et al. |
| 2004/0259736 A1 | 12/2004 | Dieing et al. |
| 2004/0266626 A1 | 12/2004 | Schrof et al. |
| 2007/0154709 A1 | 7/2007 | Koch et al. |
| 2007/0218019 A1 | 9/2007 | Andre et al. |
| 2007/0243145 A1 | 10/2007 | Andre et al. |
| 2008/0058229 A1 | 3/2008 | Berkland et al. |
| 2008/0213326 A1 | 9/2008 | Amrhein et al. |
| 2008/0213590 A1 | 9/2008 | Greiner et al. |
| 2008/0227646 A1 | 9/2008 | Martin et al. |
| 2008/0260851 A1 | 10/2008 | Somasundaran et al. |

(Continued)

FOREIGN PATENT DOCUMENTS

| | | |
|---|---|---|
| CA | 2391660 A1 | 5/2001 |
| CA | 2628836 A1 | 11/2001 |

(Continued)

OTHER PUBLICATIONS

International Search Report for PCT/IB2009/06947, 4 pages (Feb. 2, 2010).
International Search Report for PCT/IB2011/000626, 4 pages (Aug. 3, 2011).
International Search Report for PCT/IB2012/002118, 4 pages (Feb. 6, 2013).
International Search Report for PCT/IB2012/002832, 3 pages (May 17, 2013).

(Continued)

*Primary Examiner* — Susan Tran
*Assistant Examiner* — William Craigo
(74) *Attorney, Agent, or Firm* — Choate, Hall and Stewart LLP; Charles E. Lyon

(57) ABSTRACT

The present invention provides a composition including a polymer nanoparticle and at least one agricultural active compound incorporated with the nanoparticle, wherein the nanoparticle are less than 100 nm in diameter, and the polymer includes a polyelectrolyte.

15 Claims, 10 Drawing Sheets

(56) References Cited

U.S. PATENT DOCUMENTS

| | | |
|---|---|---|
| 2009/0053272 A1 | 2/2009 | Wagenblast |
| 2009/0239749 A1 | 9/2009 | Duncalf et al. |
| 2010/0016443 A1 | 1/2010 | Toledano et al. |
| 2010/0119829 A1 | 5/2010 | Karpov et al. |
| 2010/0210465 A1 | 8/2010 | Li et al. |
| 2010/0227761 A1 | 9/2010 | Bruggemann et al. |
| 2012/0065071 A1 | 3/2012 | Li et al. |
| 2013/0034650 A1 | 2/2013 | Li et al. |
| 2013/0130904 A1 | 5/2013 | Li et al. |
| 2014/0287010 A1 | 9/2014 | Li et al. |

FOREIGN PATENT DOCUMENTS

| | | | |
|---|---|---|---|
| CA | 2625880 A1 | 4/2007 | |
| CN | 102223790 A | 10/2011 | |
| IL | WO 2008032328 A2 * | 3/2008 | ............ A01N 25/04 |
| JP | 10-287506 A | 10/1998 | |
| JP | 11-222402 A | 8/1999 | |
| JP | 2002-524536 A | 8/2002 | |
| JP | 2003/514650 A | 4/2003 | |
| JP | 2004-331625 A | 11/2004 | |
| JP | 2005-504103 A | 2/2005 | |
| JP | 2005/507427 A | 3/2005 | |
| JP | 2005-526868 A | 9/2005 | |
| JP | 2007-526198 A | 9/2007 | |
| JP | 2009/512744 A | 3/2009 | |
| WO | WO-0015263 A1 | 3/2000 | |
| WO | WO-01/37803 A2 | 5/2001 | |
| WO | WO-01/90226 A1 | 11/2001 | |
| WO | WO-03/028453 A1 | 4/2003 | |
| WO | WO-03066712 A1 | 8/2003 | |
| WO | WO-03/039249 | 9/2003 | |
| WO | WO-2005/059023 A1 | 6/2005 | |
| WO | WO-2007/041862 A1 | 4/2007 | |
| WO | WO-2007/082802 A1 | 7/2007 | |
| WO | WO-2007104750 A2 | 9/2007 | |
| WO | WO-2008/099285 A2 | 8/2008 | |
| WO | WO-2009/009469 A1 | 1/2009 | |
| WO | WO-2010/035118 A1 | 4/2010 | |
| WO | WO-2010/078852 A1 | 7/2010 | |
| WO | WO-2011117719 A1 | 9/2011 | |

OTHER PUBLICATIONS

Liu, H. et al., Chitosan nanoparticles for loading of toothpaste actives and adhesion on tooth analogs, Journal of Applied Polymer Science, 106(6):4248-56 (2007).

Liu, Y. et al., Stabilized Polymeric nanoparticles for controlled and efficient release of bifenthrin, Pest Management Science, 64(8):808-812 (2008).

Molnar, R.M. Preparation and characterization of poly (acrylic acid)-based nanoparticles, Colloid and Polymer Science, 287(6):739-744 (2009).

Pham, H. et al., Polymer nanoparticles as formulation agents, Nanotechnology, 1:869-871 (2010).

Written Opinion for PCT/IB2009/06947, 4 pages (Feb. 2, 2010).
Written Opinion for PCT/IB2011/000626, 6 pages (Aug. 3, 2011).
Written Opinion for PCT/IB2012/002118, 6 pages (Feb. 6, 2013).
Written Opinion for PCT/IB2012/002832, 8 pages (May 17, 2013).

Yoksan, R. et al, Encapsulation of ascorbyl palmitate in chitosan nanoparticles by oil-in-water emulsion and ionic gelation processes, Colloids and Surfaces B: Biointerfaces, 76(1):292-7 (2010).

* cited by examiner

Figure 8 Controlled release
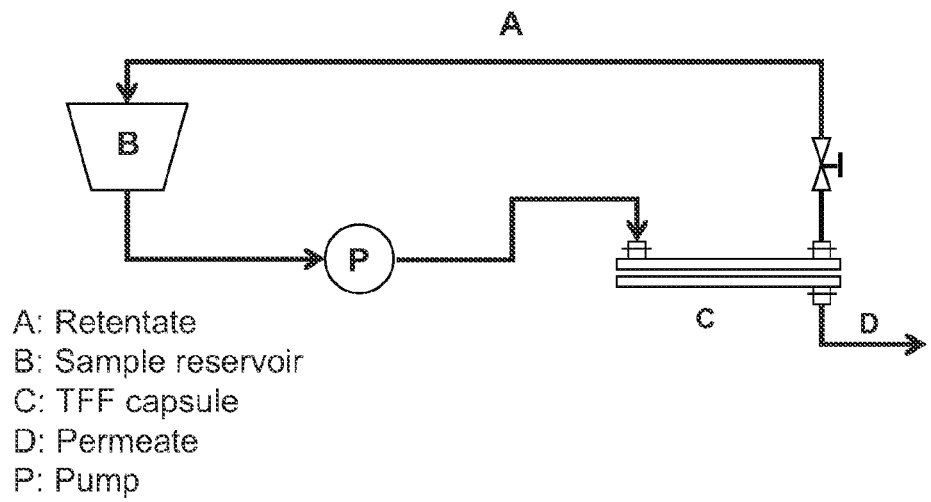
A: Retentate
B: Sample reservoir
C: TFF capsule
D: Permeate
P: Pump
A. Control release setup
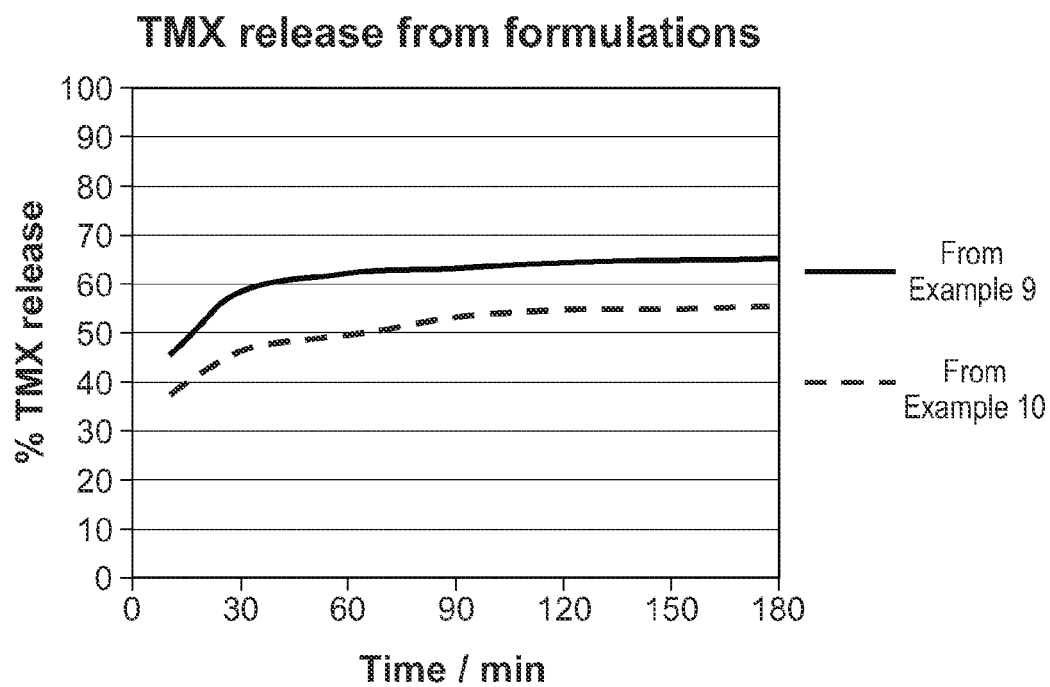
B. Slow release profile of TXM loaded nanoparticles

METHODS TO PRODUCE POLYMER NANOPARTICLES AND FORMULATIONS OF ACTIVE INGREDIENTS

RELATED APPLICATIONS

This application is a continuation of U.S. application Ser. No. 14/292,667, filed on May 30, 2014, which is a continuation of U.S. application Ser. No. 13/741,673, filed on Jan. 15, 2013 (now U.S. Pat. No. 8,741,808), which is a continuation of U.S. application Ser. No. 13/299,214, filed on Nov. 17, 2011 (now abandoned), which is a continuation of U.S. application Ser. No. 12/775,049, filed on May 6, 2010 (now U.S. Pat. No. 8,084,397), which is a continuation of International Application No. PCT/IB09/06947, filed on Sep. 25, 2009, which claims priority to U.S. Provisional Patent Application Ser. No. 61/100,068, filed on Sep. 25, 2008, and U.S. Provisional Patent Application Ser. No. 61/158,483, filed on Mar. 9, 2009, the entire contents of each of which are hereby incorporated by reference.

BACKGROUND OF THE INVENTION

Nanoparticles are nanometer-sized materials e.g., metals, semiconductors, polymers, organics, and the like, that can often posses unique characteristics because of their small size. Polymer nanoparticles of pharmaceutical or crop protection active ingredients (AIs) are of particular interest because of the potential for reduced use of formulants, improved bioavailability, modified translocation, or controlled release properties. Polymer nanoparticles with hollow interiors have found widespread use in many applications such as controlled release of drugs of pharmaceuticals, active ingredients (AIs) in agriculture, cosmetics, and foods. They are also found to protect biologically active species from degradation, and can be used remove pollutants from the environment.

SUMMARY OF THE INVENTION

The present invention encompasses the discovery that agricultural active ingredients can be associated with polymeric nanoparticles to improve the performance of the active ingredients. The present invention, among other things, provides several methods for the production and use of improved active ingredients.

In various aspects, the present invention provides compositions including a polymer nanoparticle and at least one agricultural active compound incorporated with the nanoparticle. In some embodiments, the nanoparticle is less than 100 nm in diameter. In some embodiments, the polymer includes a polyelectrolyte. In some embodiments, the agricultural active compound is an organic compound.

In some embodiments, the agricultural active compound is selected from the group consisting of an acaracide, a fungicide, a bactericide, a herbicide, an antibiotic, an antimicrobial, a nemacide, a rodenticide, an entomopathogen, a pheromone, a chemosterilant, a virus, an attractant, a plant growth regulator, an insect growth regulator, a repellent, a plant nutrient, a phagostimulant, a germicide, and combinations thereof. In some embodiments, the active ingredient is selected from the group consisting of azoxystrobin, emamectin and its salts, abermectin and its salts, thiamethoxam, glyphosate, 2,4-dichlorophenoxy)acetic acid, atrazine, picloram, imazethapyr, or thifensulfuron-methyl, and combinations thereof. In some embodiments, the active ingredient is selected from the group consisting of atrazine, neonicitinoids, photosynthesis inhibitors, amino acid synthesis inhibitors, growth regulators, pyrethrins, avermectins, and strobilurins.

In some embodiments, the nanoparticles are less than 50 nm in size. In some embodiments, the nanoparticles are less than 20 nm in size. In some embodiments, the polymer includes multiple polymer molecules. In some embodiments, the polymer nanoparticle is crosslinked. In some embodiments, the crosslinking step is accomplished by one of the following: electromagnetic radiation induced cross-linking, chemically induced cross-linking or thermally induced cross-linking.

In various embodiments, the present invention provides a dispersion including a polymer nanoparticle and at least one agricultural active compound incorporated with the nanoparticle, wherein the active ingredient is dispersed at a concentration higher than its solubility in the absence of the polymer nanoparticle In some embodiments, the polymer is selected from the group consisting of poly(acrylic acid), poly(methacrylic acid), poly (styrene sulfonate), chitosan, poly (dimethyldiallylammonium chloride), poly (allylamine hydrochloride), or copolymers or graft polymers thereof and combinations thereof.

In some embodiments, at least a portion of the active ingredient is in the interior of the polymer nanoparticle. In some embodiments, at least a portion of the active ingredient is on the surface of the polymer nanoparticle. In some embodiments, the active ingredient remains associated with the polymer nanoparticle after being exposed to a solvent In various embodiments, the present invention provides for extended or sustained release after application. In some embodiments, the trigger for release is selected from the group consisting of pH change, temperature change, barometric pressure change, osmotic pressure change, exposure to water, exposure to a solvent, changes in shear forces, application of the formulation, exposure to a bacteria, exposure to an enzyme, exposure to electromagnetic radiation and exposure to free radicals. In some embodiments, the active ingredient is released via triggered release. In some embodiments, the polymer nanoparticle has a cavity. In some embodiments, the polymer nanoparticle has a network structure. In some embodiments, the active ingredient associated with the polymer nanoparticle has different mobility in soil than it has when not associated with the polymer nanoparticle. In some embodiments, polymer has hydrophilic and hydrophobic regions. In some embodiments, the polymer nanoparticles can be recovered in a dried form and redispersed in a suitable solvent.

In some embodiments, the active ingredient isazoxystrobin, emamectin and its salts, abermectin and its salts, thiamethoxam, glyphosate, 2,4-dichlorophenoxy)acetic acid, atrazine, picloram, imazethapyr, or thifensulfuron-methyl, and combinations thereof. In some embodiments, the active ingredient is atrazine, neonicitinoids, photosynthesis inhibitors, amino acid synthesis inhibitors, growth regulators, pyrethrins, avermectins, and strobilurins.

In various aspects, the present invention provides a method to make polymer nanoparticles, including the steps of dissolving a polyelectrolyte into an aqueous solution under solution conditions that render it charged, adding a species that is oppositely charged under these conditions to cause the polymer to collapse, and crosslinking the polymer. In some embodiments, the crosslinking step is accomplished by one of the following: electromagnetic radiation induced cross-linking, chemically induced cross-linking or thermally induced cross-linking.

In some embodiments, the oppositely charged species is an active ingredient.

In some embodiments, the oppositely charged species is removed from the polymer nanoparticle. In some embodiments, the oppositely charged species is removed from the polymer nanoparticle by pH adjustment, filtration, dialysis, or combinations thereof.

In some embodiments, the method further includes the step of associating an active ingredient with the polymer nanoparticle.

In some embodiments, the method includes the step of removing the solvent. In some embodiments, the solvent is removed by lyophilization, distillation, extraction, selective solvent removal, filtration, dialysis, or evaporation. In some embodiments, the method includes the step of redispersing the nanoparticles in a suitable solvent.

In some embodiments, the method includes an agricultural active compound selected from the group consisting of an acaracide, a fungicide, a bactericide, a herbicide, an antibiotic, an antimicrobial, a nemacide, a rodenticide, an entomopathogen, a pheromone, a chemosterilant, a virus, an attractant, a plant growth regulator, an insect growth regulator, a repellent, a plant nutrient, a phagostimulant, a germicide, and combinations thereof.

In some embodiments, the method includes a nanoparticles are less than 50 nm in size. In some embodiments, the method includes a nanoparticles are less than 20 nm in size. In some embodiments, the method includes multiple polymer molecules. In some embodiments, the method includes a polymer nanoparticle that is crosslinked In some embodiments, the method includes a polymer that is selected from the group consisting of poly(acrylic acid), poly(methacrylic acid), poly (styrene sulfonate), chitosan, poly (dimethyldiallylammonium chloride), poly (allylamine hydrochloride), or copolymers or graft polymers thereof and combinations thereof. In some embodiments, the method includes a portion of the active ingredient is on the surface of the polymer nanoparticle.

In some embodiments, the method includes an associating step which itself includes the steps of dissolving the polymer nanoparticles in a suitable first solvent, swelling the polymer nanoparticles by adding a second solvent containing active ingredient, and removing the second solvent.

In some embodiments, the method includes an associating step which itself includes the steps of dissolving the polymer nanoparticles and active ingredient in a suitable first solvent, adding a second solvent, and removing the first solvent.

In some embodiments, the method includes an associating step which itself includes the steps of dissolving the polymer nanoparticles and active ingredient in a suitable solvent, and removing the solvent.

In various aspects, the present invention provides a method to associate an active ingredient with a polymer nanoparticle, including the steps of dissolving the polymer nanoparticles in a suitable first solvent, swelling the polymer nanoparticles by adding a second solvent containing active ingredient, and removing the second solvent.

In various aspects, the present invention provides a method to associate active ingredient with polymer nanoparticles including the steps of dissolving the polymer nanoparticles and active ingredient in a suitable first solvent, adding a second solvent and removing the first solvent.

In various aspects, the present invention provides a method to associate active ingredient with polymer nanoparticles including the steps of dissolving the polymer nanoparticles and active ingredient in a suitable solvent and removing the solvent.

In some embodiments of the method, the first solvent is water. In some embodiments of the method, the second solvent is not miscible in the first solvent. In some embodiments of the method, the second solvent is partially miscible in the first solvent In various aspects, the present invention provides, a method to make polymer nanoparticles including active ingredient, including the steps of dissolving a polyelectrolyte in a suitable solvent, associating an active ingredient with the polyelectrolyte, and collapsing the polyelectrolyte.

In some embodiments, the association of the active ingredient with the polyelectrolyte causes the collapse of the polyelectrolyte. In some embodiments, the collapse is caused by a change in solvent conditions, by a change in temperature, by a change in pH.

In some embodiments, the polymer nanoparticles including active ingredient are crosslinked. In some embodiments, the active ingredient is chemically modified.

In various aspects, the present invention provides a method of using a composition including a polymer nanoparticle and at least one agricultural active compound incorporated with the nanoparticle by applying the composition to a plant, a seed, or soil. In some embodiments, the composition of is sprayed as an aerosol on the crop. In some embodiments, the composition is part of a formulation with other ingredients in solution. In some embodiments, the method of treatments is essentially free of added surfactants.

BRIEF DESCRIPTION OF THE DRAWINGS

FIG. 8 shows exemplary controlled release test apparatus and test results. A. Control release experimental setup. B. Control release characteristics of TMX.

DESCRIPTION OF VARIOUS EMBODIMENTS

Figure 1:
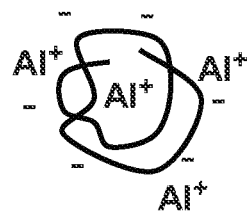
FIG. 1 is an illustration of exemplary polymer nanoparticles comprising active ingredients. Active ingredients can be associated with the nanoparticle inside, or on the surface.

In various aspects, the present invention describes methods of producing polymer particles and polymer gel particles with an average size ranging from 1 nm to 800 nm, using polyelectrolytes. These particles are generally spherical (e.g., elliptical, oblong, etc.) in shape, swollen or not swollen, may be hollow in the center, or may contain cavities. The particles may include active ingredients.

Prior to further describing the present inventions, it may be helpful to provide a general discussion of the usage of terms herein.

As used herein, the term "active ingredients" refer to an active compound or a mixture of active compounds in pesticide formulations, or to an active pharmaceutical ingredient or a mixture of active pharmaceutical ingredients. It can also include substances with biological activity which are not typically considered to be active ingredients, such as fragrances, flavor compounds, hormones, homo, oligo, or poly nucleic acids or peptides, and the like.

Exemplary classes of active ingredient for the present invention include acaricides, algicides, avicides, bactericides, fungicides, herbicides, insecticides, miticides, molluscicides, nematicides, rodenticides, virucides, algicides, bird repellents, mating disrupters, plant activators, antifeedants, insect attractants and repellants.

Active ingredients of herbicides can function as, amino acid synthesis inhibitors, cell membrane disrupters, lipid synthesis inhibitors, pigment inhibitors, seedling growth inhibitors, growth regulators, photosynthesis inhibitors.

Examples of active ingredients as amino acid synthesis inhibitors include, but not limited to, imazethapyr (2-[4,5-dihydro-4-methyl-4-(1-methylethyl)-5-oxo-1H-imidazol-2-yl]-5-ethyl-3-pyridinecarboxylic acid), thifensulfuron (3-[[[[(4-methoxy-6-methyl-1,3,5-triazin-2-yl)amino] carbonyl]amino]sulfonyl]-2-thiophenecarboxylic acid), thifensulfuron-methyl (methyl 3-[[[[(4-methoxy-6-methyl-1,3,5-triazin-2-yl)amino]carbonyl]amino]sulfonyl]-2-thiophenecarboxylate), glyphosate (N-(phosphonomethyl)glycine).

Examples of active ingredients as cell membrane disrupters include, but not limited to, diquat (6,7-dihydrodipyrido [1,2-a:2',1'-c]pyrazinediium), paraquat (1,1'-dimethyl-4,4'-bipyridinium).

Examples of active ingredients as lipid synthesis inhibitors include, but not limited to, clodinafop propargyl (2-propynyl (2R)-2-[4-[(5-chloro-3-fluoro-2-pyridinyl)oxy]phenoxy]propanoate), tralkoxydim (2-[1-(ethoxyimino)propyl]-3-hydroxy-5-(2,4,6-trimethylphenyl)-2-cyclohexen-1-one).

Examples of active ingredients as pigment inhibitors include, but not limited to, mesotrione (2-[4-(methylsulfonyl)-2-nitrobenzoyl]-1,3-cyclohexanedione), clomazone (2-[(2-chlorophenyl)methyl]-4,4-dimethyl-3-isoxazolidinone).

Examples of active ingredients as seedling growth inhibitors include, but not limited to, metolachlor (2-chloro-N-(2-ethyl-6-methylphenyl)-N-(2-methoxy-1-methylethyl)acetamide), triflualin (2,6-dinitro-N,N-dipropyl-4-(trifluoromethyl)benzenamine), diflufenzopyr (2-[1-[[[(3,5-difluorophenyl)amino]carbonyl]hydrazono]ethyl]-3-pyridinecarboxylic acid).

Examples of active ingredients as growth regulators include, but not limited to, 2,4-D (2,4-dichlorophenoxy) acetic acid), dicamba (3,6-dichloro-2-methoxybenzoic acid), MCPA ((4-chloro-2-methylphenoxy)acetic acid), picloram (4-amino-3,5,6-trichloro-2-pyridinecarboxylic acid), triclopyr ([(3,5,6-trichloro-2-pyridinyl)oxy]acetic acid).

Examples of active ingredients as photosynthesis inhibitors include, but not limited to, atrazine (6-chloro-N-ethyl-N'-(1-methylethyl)-1,3,5-triazine-2,4-diamine), metribuzin (4-amino-6-(1,1-dimethylethyl)-3-(methylthio)-1,2,4-triazin-5(4H)-one), bromacil (5-bromo-6-methyl-3-(1-methylpropyl)-2,4(1H,3H)-pyrimidinedione), tebuthiuron (N-[5-(1,1-dimethylethyl)-1,3,4-thiadiazol-2-yl]-N,N'-dimethylurea), propanil (N-(3,4-dichlorophenyl) propanamide), bentazon (3-(1-methylethyl)-1H-2,1,3-benzothiadiazin-4(3H)-one 2,2-dioxide), bromoxynil (3,5-dibromo-4-hydroxybenzonitrile), pyridate (O-(6-chloro-3-phenyl-4-pyridazinyl) S-octyl carbonothioate).

Active ingredients of insecticides can function as, acetylcholinesterase inhibitors, GABA-gate chloride channel antagonists, sodium channel modulators, nicotinic acetylcholine receptor agonists, chloride channel activators, juvenile hormone mimics, non-specific (multi-site) inhibitors, selective homopteran feeding blockers, mite growth inhibitors, inhibitors of mitochondrial ATP synthase, uncouplers of oxidative phosphorylation via disruption of the proton gradient, nicotinic acetylcholine receptor channel blockers, inhibitors of chitin biosynthesis (type 0 and 1), moulting disruptor, ecdysone receptor agonists, octopamine receptor agonists, mitochondrial complex I electron transport inhibitors, mitochondrial complex III electron transport inhibitors, mitochondrial complex IV electron transport inhibitors, voltage-dependent sodium channel blockers, inhibitors of acetyl CoA carboxylase, ryanodine receptor modulators.

Examples of active ingredients as acetylcholinesterase inhibitors include, but not limited to, carbamates (e.g. carbofuran (2,3-dihydro-2,2-dimethyl-7-benzofuranyl methylcarbamate), carbosulfan (2,3-dihydro-2,2-dimethyl-7-benzofuranyl [(dibutylamino)thio]methylcarbamate)) and organophosphates chemicals (e.g. chlorpyrifos-methyl (O,O-dimethyl O-(3,5,6-trichloro-2-pyridinyl) phosphorothioate)).

Examples of active ingredients as GABA-gate chloride channel antagonists include, but not limited to, chlordane (1,2,4,5,6,7,8,8-octachloro-2,3,3a,4,7,7a-hexahydro-4,7-methano-1H-indene), endosulfan (6,7,8,9,10,10-hexachloro-1,5,5a,6,9,9a-hexahydro-6,9-methano-2,4,3-benzodioxathiepin 3-oxide), ethiprole (5-amino-1-[2,6-dichloro-4-(trifluoromethyl)phenyl]-4-(ethylsulfinyl)-1H-pyrazole-3-carbonitrile), fipronil (5-amino-1-[2,6-dichloro-4-(trifluoromethyl)phenyl]-4-[(trifluoromethyl)sulfinyl]-1H-pyrazole-3-carbonitrile).

Examples of active ingredients as sodium channel modulators include, but not limited to, DDT (1,1'-(2,2,2-trichloroethylidene)bis[4-chlorobenzene]), methoxychlor (1,1'-(2,2,2-trichloroethylidene)bis[4-methoxybenzene]), pyrethrin compounds (e.g. bifenthrin ((2-methyl[1,1'-biphenyl]-3-yl) methyl (1R,3R)-rel-3-[(1Z)-2-chloro-3,3,3-trifluoro-1-propenyl]-2,2-dimethylcyclopropanecarboxylate), lambda-cyhalothrin ((R)-cyano(3-phenoxyphenyl)methyl (1S,3S)-rel-3-[(1Z)-2-chloro-3,3,3-trifluoro-1-propenyl]-2,2-dimethylcyclopropanecarboxylate), pyrethrins ((RS)-3-allyl-2-methyl-4-oxocyclopent-2-enyl (1R,3R)-2,2- dimethyl-3-(2-methylprop-1-enyl) cyclopropanecarboxylate), tetramethrin ((1,3,4,5,6,7-hexahydro-1,3-dioxo-2H-isoindol-2-yl)methyl 2,2-dimethyl-3-(2-methyl-1-propenyl) cyclopropanecarboxylate), Examples of active ingredients as nicotinic acetylcholine receptor agonists include, but not limited to, nicotine and neonicotinoids (e.g. acetamiprid, imidacloprid, thiamethoxam).

Examples of active ingredients as chloride channel activators include, but not limited to, milbemycins (e.g. milbemectin ((6R,25R)-5-O-demethyl-28-deoxy-6,28-epoxy-25-ethylmilbemycin B mixture with (6R,25R)-5-O-demethyl-28-deoxy-6,28-epoxy-25-methylmilbemycin B) and avermectins (e.g. abamectin (mixture of 80% (2aE,4E,8E)-(5'S,6S,6'R,7S,11R,13S,15S,17aR,20R,20aR,20bS)-6'-[(S)-sec-butyl]-5',6,6',7,10,11,14,15,17a,20,20a,20b-dodecahydro-20,20b-dihydroxy-5',6,8,19-tetramethyl-17-oxospiro[11,15-methano-2H,13H,17H-furo[4,3,2-pq][2,6]benzodioxacyclooctadecin-13,2'-[2H]pyran]-7-yl 2,6-dideoxy-4-O-(2,6-dideoxy-3-O-methyl-α-L-arabino-hexopyranosyl)-3-O-methyl-α-L-arabino-hexopyranoside and 20% (2aE,4E,8E)-(5'S,6S,6'R,7S,11R,13S,15S,17aR,20R,20aR,20bS)-5',6,6',7,10,11,14,15,17a,20,20a,20b-dodecahydro-20,20b-dihydroxy-6'-isopropyl-5',6,8,19-tetramethyl-17-oxospiro[11,15-methano-2H,13H,17H-furo[4,3,2-pq][2,6]benzodioxacyclooctadecin-13,2'-[2H]pyran]-7-yl 2,6-dideoxy-4-O-(2,6-dideoxy-3-O-methyl-α-L-arabino-hexopyranosyl)-3-O-methyl-α-L-arabino-hexopyranoside, or avermectin B1), emamectin benzoate ((4'R)-4'-deoxy-4'-(methylamino)avermectin B1 benzoate (salt)).

Examples of active ingredients as inhibitors of mitochondrial ATP synthase include, but not limited to, diafenthiuron (N-[2,6-bis(1-methylethyl)-4-phenoxyphenyl]-N'-(1,1-dimethylethyl)thiourea), propargite (2-[4-(1,1-dimethylethyl) phenoxy]cyclohexyl 2-propynyl sulphite), tetradifon (1,2,4-trichloro-5-[(4-chlorophenyl)sulfonyl]benzene).

Examples of active ingredients as inhibitors of chitin biosynthesis (type 0) include, but not limited to, benzoylureas (e.g. bistrifluron (N-[[[2-chloro-3,5-bis(trifluoromethyl)phenyl]amino]carbonyl]-2,6-difluorobenzamide), diflubenzuron (N-[[(4-chlorophenyl)amino]carbonyl]-2,6-difluorobenzamide), teflubenzuron (N-[[(3,5-dichloro-2,4-difluorophenyl)amino]carbonyl]-2,6-difluorobenzamide).

Examples of active ingredients as inhibitors of acetyl CoA carboxylase include, but not limited to, tetronic and tetramic acid derivatives (e.g. spirodiclofen (3-(2,4-dichlorophenyl)-2-oxo-1-oxaspiro[4.5]dec-3-en-4-yl 2,2-dimethylbutanoate)).

Active ingredients of fungicides can target, nucleic acid synthesis, mitosis and cell division, respiration, protein synthesis, signal transduction, lipids and membrane synthesis, sterol biosynthesis in membranes, glucan synthesis, host plant defence induction, multi-site contact activity, and other unknown mode of action.

Examples of active ingredients targeted at nucleic acids synthesis include, but not limited to, acylalanines (e.g. metalxyl-M (methyl N-(2,6-dimethylphenyl)-N-(methoxyacetyl)-D-alaninate)), isothiazolones (e.g. octhilinone (2-octyl-3(2H)-isothiazolone)).

Examples of active ingredients targeted at mitosis and cell division include, but not limited to, benzimidazoles (e.g. thiabendazole (2-(4-thiazolyl)-1H-benzimidazole)), thiophanates (e.g. thiophanate-methyl (dimethyl [1,2-phenylenebis(iminocarbonothioyl)]bis[carbamate])), toluamides (e.g. zoxamide (3,5-dichloro-N-(3-chloro-1-ethyl-1-methyl-2-oxopropyl)-4-methylbenzamide)), pyridinylmethyl-benzamides (e.g. fluopicolide (2,6-dichloro-N-[[3-chloro-5-(trifluoromethyl)-2-pyridinyl]methyl]benzamide)).

Examples of active ingredients targeted at respiration include, but not limited to, carboxamide compounds (e.g. flutolanil (N-[3-(1-methylethoxy)phenyl]-2-(trifluoromethyl)benzamide), carboxin (5,6-dihydro-2-methyl-N-phenyl-1,4-oxathiin-3-carboxamide)), strobilurin compounds (e.g. azoxystrobin (methyl (αE)-2-[[6-(2-cyanophenoxy)-4-pyrimidinyl]oxy]-α-(methoxymethylene)benzeneacetate), pyraclostrobin (methyl [2-[[[1-(4-chlorophenyl)-1H-pyrazol-3-yl]oxy]methyl]phenyl]methoxycarbamate), trifloxystrobin (methyl (αE)-α-(methoxyimino)-2-[[[[(1E)-1-[3-(trifluoromethyl)phenyl]ethylidene]amino]oxy]methyl] benzeneacetate), fluoxastrobin ((1E)-[2-[[6-(2-chlorophenoxy)-5-fluoro-4-pyrimidinyl]oxy]phenyl](5,6-dihydro-1,4,2-dioxazin-3-yl)methanone O-methyloxime)).

Examples of active ingredients targeted at multi-site contact activity include, but not limited to, dithiocarbamate compounds (e.g. thiram (tetramethylthioperoxydicarbonic diamide)), phthalimide compounds (e.g. captan (3a,4,7,7a-tetrahydro-2-[(trichloromethyl)thio]-1H-isoindole-1,3(2H)-dione)), chloronitrile compounds (e.g. chlorothalonil (2,4,5,6-tetrachloro-1,3-benzenedicarbonitrile)).

As used herein, the term "polyelectrolytes" refers to polymers containing ionized or ionizable groups. The ionized or ionizable groups can be eithercationic, anionic, or zwitterionic. Preferred cationic groups are the amino or quaternary ammonium groups while preferred anionic groups are carboxylate, sulfonate and phosphates. Polyelectrolytes can be homopolymers, copolymers (random, alternate, graft or block). They can be synthesized or naturally occurred, and can be linear, branched, hyperbranched, or dendrimeric. For cationic polymers, examples include, but are not limited to, poly(allyamine), poly(ethyleneimine) (PEI), poly(diallydimethylammonium chloride) (PDDA), poly(lysine), chitosan or a mixture of any of polycationic polymers. For anionic polymers, examples include, but are not limited to, poly(acrylic acid) (PAA), poly(methacrylic acid) (PMA), poly(styrene sulfonic acid) (PSS), poly(glutamic acid), alginic acid, carboxymethylcellulose (CMC), humic acid, or a mixture of polyanionic polymers.

As used herein, the term "medium" refers to a solvent (or a mixture of solvents) used to form a polymeric solution. Solvents can be homogeneous or heterogeneous, but are not limited to, water, organic, perfluorinated, ionic liquids, or liquid carbon dioxide ($CO_2$), or a mixture of solvents, amongst others. In various embodiments, the solvent is water.

Compositions

In one aspect, the present invention provides for polymer nanoparticles comprising active ingredients. FIG. 1 illustrates an exemplary nanoparticle-active ingredient composition. The polymer nanoparticle-active ingredient composite can have improved physical and chemical features that are not found in the components alone. For example, the polymer nanoparticles can improve the water solubility of the active ingredient without effecting the active ingredient's efficacy. In some embodiments, the polymer nanoparticles can increase or decrease the soil mobility of the active ingredient as compared to the active ingredient by itself, or as in typical active ingredient formulations. In some embodiments, the polymer nanoparticles can be used to control soil mobility to a targeted region of the soil. Several active ingredients, while generally effective for their indicated use, suffer from inefficiencies in use because of low water solubility, leaf spreading (or wettability on leaf surface), cuticle penetration or generally poor translocation through the plant. This requires the use of additional compounds in the formulation and higher concentrations of the active ingredient. Active ingredient formulations typically utilize surfactants (e.g., amine ethoxylates) and organic solvents to overcome these problems, however, these surfactants and organic solvents can have toxicological, environmental or other negative consequences. Polymer nanoparticles comprising active ingredients in this invention can reduce or even eliminate the need for surfactants, organic solvents, and lower the concentration requirements of the active ingredient while keeping the level of efficacy similar.

The polymer nanoparticles may comprise polyelectrolytes and may be prepared according to the methods of the current invention. The polymer nanoparticles may comprise one or more polymer molecules, which may be the same type of polymer or different polymers. The molecular weight of the polymer or polymers in the polymer nanoparticle can be approximately between 100,000 and 250,000 Dalton, approximately more than 250,000 Dalton, approximately between 5,000 and 100,000 Dalton, or approximately less than 5,000 Dalton. If multiple polymers are used, they can be dissimilar in molecular weight; as an example, the polymer nanoparticle can comprise high molecular weight and low molecular weight poly(acrylic acid) polymers.

The molecular weight difference can be effective if the low molecular weight polymer and the high molecular weight polymer have complementary functional groups; e.g. the ability to participate in 'Click' chemistry as described below. In this case, the low molecular weight polymer is acting as a cross-linker of the high molecular weight polymer in the nanoparticle.

The polymer nanoparticles may be cross-linked, either chemically or with light or with particulate irradiation (e.g. gamma irradiation). The density of cross-linking can be modified to control the transport of material from the interior of the polymer nanoparticle to the environment of the nanoparticle. The polymer nanoparticle may comprise discrete cavities in its interior, or may be a porous network. In various embodiments, the nanoparticle has a mean diameter in one or more of the ranges between: about 1 nm to about 10 nm; about 10 nm to about 30 nm; about 15 nm to about 50 nm; and about 50 nm to about 100 nm; about 100 nm to about 300 nm). It is to be understood that the term "mean diameter" is not meant to imply any sort of specific symmetry (e.g., spherical, ellipsoidal, etc.) of a composite nanoparticle. Rather, the nanoparticle could be highly irregular and asymmetric.

The polymer nanoparticle can comprise hydrophilic (ionized, ionizable, or polar non-charged) and hydrophobic regions. If the polymer nanoparticle comprises a polyelectrolyte in a polar or hydrophilic solvent, the polyelectrolyte can organize itself so that its surface is enriched with ionized or ionizable groups and its interior is enriched with hydrophobic groups. This can occur in relatively hydrophilic or polar solvents. In hydrophobic solvents, the inverse process can occur; that is, that the polyelectrolyte can organize itself so that its surface is enriched with hydrophobic groups and its interior is enriched with ionized or ionizable groups. This effect can be enhanced by appropriate choice of polyelectrolytes with hydrophilic and hydrophobic regions; it can also be enhanced by modification of the polyelectrolyte e.g., adding hydrophobic regions to the polyelectrolyte.

Modification of the polymer can be performed by various methods, including conjugation, copolymerization, grafting and polymerization, or by exposure to free radicals. Modification can be designed before, during or after the preparation of polymer nanoparticles. An example of polymer modification during the preparation of polymer nanoparticles involves with poly(acrylic acid). Under appropriate conditions, poly(acrylic acid) that is exposed to UV will decarboxylate some of its acid groups, thereby increasing the hydrophobicity of the system. Similar treatment can be used with other types of polymers. Modification of the polymer can be observed using titration, spectroscopy or nuclear magnetic resonance (NMR) under suitable conditions. Polymer modification can also be observed using size exclusion or affinity chromatography. The hydrophobic and hydrophilic regions of the polymer nanoparticle can be observed using solvent effects. If the nanoparticle is dispersible in a first polar solvent such as water, it is clear that it must have exposed surface hydrophilicity. This can also be ascertained using surface charge analysis such as a zeta potential measurement. If it is also possible to swell the polymer through addition of a miscible, partially miscible, or non-miscible second solvent that is more hydrophobic than the first polar solvent, this demonstrates the existence of hydrophobicity in the interior of the nanoparticle. Swelling can be observed through a change in particle size observed using light scattering or by disappearance of an immiscible second solvent phase due to partitioning of the solvent into the nanoparticle. The inverse experiment with a first hydrophobic solvent and a second hydrophilic solvent can be used to observe enrichment in hydrophobic groups on the surface of the nanoparticle and hydrophilic groups in the interior of the nanoparticle.

The polymer nanoparticle of the present invention comprises active ingredients. The active ingredients can be covalently bound to the polymer or physically associated with the polymer. An example method to produce polymer nanoparticle containing active ingredients chemically bound to the polymer has been described elsewhere in this specification. The active ingredients can also be physically or chemically associated with the polymer of the polymer nanoparticle in a non-covalent fashion. If the polymer nanoparticle comprises multiple polymers, the active ingredients can be physically or chemically associated with one or multiple polymers in the polymer nanoparticles. Physical association is defined by non-covalent interactions such as charge-charge interactions, hydrophobic interactions, polymer-chain entanglement, affinity pair interactions, hydrogen bonding, van der Waals forces, or ionic interactions.

Alternatively, there can be little interaction between the active ingredient and the polymer nanoparticle but the active ingredient can be trapped inside or associated with the polymer nanoparticle because it is physically precluded (e.g. sterically) from escaping from the polymer nanoparticle. The active ingredient can be primarily in the interior of the polymer nanoparticle, on the surface of the polymer nanoparticle, or throughout the polymer nanoparticle. If the polymer nanoparticle has cavities, the active ingredient can be primarily inside the cavities. If the polymer nanoparticle has hydrophobic regions, the active ingredient can be associated with the hydrophobic regions or the non-hydrophobic regions, depending on the chemical identity of the active ingredient.

The present invention also provides for formulations of polymer nanoparticles comprising active ingredients. The polymer nanoparticles comprising active ingredients of the present invention can be formulated in a variety of ways. In some cases they can be dried into a solid by freeze drying, spray drying, tray drying, air drying, vacuum drying, or other drying methods. Once dried, they can be stored for some length of time and then re-suspended into a suitable solvent when they need to be used. In certain embodiments, the dried solid can be granulated, made into tablets, for handling.

In some embodiments, polymer nanoparticles comprising active ingredient in a solvent can be formulated into a gel. This can be done by removing the solvent until gelation occurs. In some embodiments, this solvent is aqueous. Once gelation occurs, the resulting gel can be stored and delivered directly or redispersed into solvent by addition of solvent. In some embodiments, polymer nanoparticles comprising active ingredients can be formulated into a suspension, dispersion, or emulsion. This can be done using standard formulation techniques known in the art.

In some embodiments, the polymer nanoparticle can provide enhanced solubility, dispersibility, stability, or other functionality to the active ingredient associated with it. One example of this would be when a polyelectrolyte-based polymer nanoparticle comprising active ingredient is dispersed in an aqueous solvent. If the active ingredient has a lower solubility than the polyelectrolyte, its association with the polyelectrolyte nanoparticle can increase its ability to be dissolved or dispersed in the solvent. This is particularly beneficial for poorly water soluble active ingredients where a formulation or use require increased water solubility or dispersibility. In certain cases, because the polymer nanoparticle provides additional solubility, dispersibility, stability, or other functionality to the active ingredient, it is possible to reduce or eliminate the use of certain formulation additives such as formulants, surfactants, dispersants, or adjuvants. In various embodiments, the resulting system does not need added surfactant. The polymer nanoparticles that the active ingredient is associated with may have both anionic and nonionic surfactant components. These will mean that the nanoparticles may have excellent penetration through the leaf cuticle. Surfactants with tunable poly(ethylene oxide) moieties may decrease the amount of glyphosate necessary for weed control substantially. This increased efficacy can arise from improved cuticle penetration due to increased hydration and increased movement (translocation) through the plant.

Furthermore, the amount of active ingredient applied can be increased in hard water applications, particularly for charged active ingredients such as glyphosate. This is because the active ingredient can be deactivated by hard water ions, so that more active ingredient needs to be applied to have the same efficacy. If the polymer nanoparticle has ionized or ionizable groups, it will be a natural hard water ion scavengers. In various embodiments, at 700 ppm hard water they will scavenge essentially all of the hard water ions at typical application rates.

In some embodiments, polymer nanoparticles comprising active ingredients enhance physical and chemical characteristics of the actives, including, e.g. soil mobility and water solubility. In certain embodiments, polymer nanoparticles comprising active ingredients can increase soil mobility of the actives. The poor soil mobility of the actives can be caused by binding of the active ingredient to a soil surface or organic matters, or by poor diffusion of the active ingredient due to poor water solubility. By providing a polymer nanoparticle comprising the active ingredient, soil mobility may be enhanced. If the polymer nanoparticle comprising the active ingredient is water soluble or dispersible, it can provide enhanced diffusion through a soil column. This can be enhanced if the polymer nanoparticle is stable and does not stick to the surface of soil particles or organic matter in the soil. This effect can be caused by several phenomena, including increased water solubility or dispersibility relative to the active ingredient without polymer nanoparticles, increased diffusion through the soil column due to small particle size relative to the pores in the soil.

In certain embodiments, the binding of the polymer nanoparticle can also be tuned or modified. This can be accomplished by modification of the surface chemistry of the polymer. Soil contains different charged moieties, which can include negative and positive moieties, depending on the soil. The interaction of the polymer nanoparticle with the soil surface can be tailored by using different polyelectrolytes or blends of polymers. By changing the polymer composition of the nanoparticle, its affinity for soil surfaces can change and thus the mobility of the nanoparticle will change. As an example, if the polymer comprises groups with a high affinity for soil surfaces, they can be modified with e.g. a non-ionic surfactant-type polymer that will help to decrease their affinity for soil surfaces. Alternately, if the polymer does not comprise groups with a high affinity for soil surfaces, but it is desired to immobilize the nanoparticles in the soil, they polymer can be modified with groups with a high affinity for soil surfaces. Such groups can include but are not limited to amines, amides, quaternary ammoniums, or in certain conditions carboxyls. This can also be accomplished by providing a polymer nanoparticle comprising active ingredient that already has chemical groups with a high affinity for soil surfaces.

The polymer nanoparticles with active ingredient can also be manipulated to have triggered, slow, or controlled release of the active ingredient. If the polymer nanoparticles are formulated in a suitable solvent, release of the active ingredient from the polymer nanoparticles can occur in several ways. First, the release can be diffusion mediated. The rate of diffusion mediated release can be modified by increasing or decreasing the density of crosslinking of the polymer nanoparticle. The rate can also be modified depending on the location of the active ingredient in the polymer nanoparticle; that is, whether it is primarily in the interior of the polymer nanoparticle, primarily on the surface of the polymer nanoparticle, or dispersed throughout the polymer nanoparticle.

In certain embodiments, if there is active ingredient on the surface of the polymer nanoparticle and in the interior of the polymer nanoparticle, release can have two stages; a 'burst' release associated with release of the active ingredient on the surface of the polymer nanoparticle, followed by a slower diffusion-mediated release of active ingredient from the interior of the nanoparticle. Release rates will also be dependent on whether the active ingredient has a chemical affinity or association for the polymer or polymers that comprise the polymer nanoparticle. Stronger chemical affinity or association between active ingredient and polymer nanoparticles indicates slower release of active ingredient from polymer nanoparticles, or vice-versa. Therefore polymer nanoparticles with varied hydrophobicilty can be tailored by chemical modifications to meet the requirement of loading active ingredients with different hydrophobicity based on the principle of "like dissolves like".

In some cases, the release of the nanoparticle can be triggered. Triggering mechanisms can include but are not limited to changes in pH, solvent conditions, addition or removal of salt, changes in temperature, changes in osmotic or barometric pressure, presence of light, or addition of polymer degrading agents like enzymes, bacteria, and free radicals. As an example, if the polymer nanoparticle comprises a polyacid, and the pH of the environment of the nanoparticle changes, the polyacid may change from its protonated to its unprotonated state or vice-versa. This may modify the affinity of the active ingredient associated with the polymer nanoparticle with the polymer. If the affinity decreases, this may lead to triggered release of the active ingredient. Changes in the surrounding salt or ion concentration as well as changes in the surrounding temperature and pressure can cause reorganization of the polymer comprising the nanoparticle. The polymer reorganization can displace the associated active ingredient towards the exterior of the nanoparticle. Exposure of the nanoparticles to light (e.g., UV radiation) or other polymer degradation agents like enzymes and free radicals can initiate the release of the active ingredient though polymer degradation. Release of active ingredient from the nanoparticle can be observed by measuring the amount of active ingredient associated with the nanoparticle and comparing it to the amount of active ingredient 'free' in the nanoparticle's environment. This can be done by separately sampling the nanoparticles and their environment; i.e. by separating the nanoparticles by e.g. membrane filtration and then measuring the active ingredient in each fraction by HPLC or UV spectroscopy. One method to do this comprises the use of a tangential flow filtration capsule, as described in the Examples. In some cases, the active ingredient associated with the nanoparticles will need to be extracted by addition of solvent.

Polymer Collapse

The conformation of a polymer in solution is dictated by various conditions of the solution, including its interaction with the solvent, its concentration, and the concentration of other species that may be present. The polymer can undergo conformational changes depending on the pH, ionic strength, cross-linking agents, temperature and concentration. For polyelectrolytes, at high charge density, e.g., when "monomer" units of the polymer are fully charged, an extended conformation is adopted due to electrostatic repulsion between similarly charged monomer units. Decreasing the charge density of the polymer, either through addition of salts or a change of pH, can result in a transition of extended polymer chains to a more tightly-packed globular i.e. collapsed conformation. The collapse transition is driven by attractive interactions between the polymer segments that override the electrostatic repulsion forces at sufficiently small charge densities. A similar transition can be induced by changing the solvent environment of the polymer. This collapsed polymer is itself of nanoscale dimensions and is, itself, a nanoparticle. Similar collapse transitions can be driven for uncharged polymers using changes in solution condition, e.g., for polymers with low critical solution temperatures such as poly-(n-isopropylacrylamide) ("NIPAM"). Alternately, collapse of an uncharged polymer can be caused by addition of a non-solvent under appropriate conditions. In this specification and claims the term "collapsed polymer" refers to an approximately globular form, generally as a spheroid, but also as an elongate or multi-lobed conformation collapsed polymer having nanometer dimensions. This collapsed conformation can be rendered permanent by intra-particle cross-linking. The cross-linking chemistry includes hydrogen bond formation, chemical reaction to form new bonds, or coordination with multivalent ions. Crosslinkers can be added after the polymer is collapsed.

Conjugation

A fraction of the functional groups of a polymer such as a polyelectrolyte can be used for conjugation or can be converted to other functional groups. These functional group scan be utilized for, e.g., cross-linking, attachment sites, polymerization, intra- and inter-particle stabilization, among other uses. For example, a bifunctional molecule, 2-hydroxyethyl methacrylate (HEMA) containing an alcohol group and a latent methacrylate group can be reacted with a carboxylic acid group of poly(acrylic acid) (PAA) through ester bond formation, converting the carboxylic acid group to a methacrylate group. The methacrylate group can be crosslinked when exposed to UV radiation or an elevated temperature. As a result, a number of methacrylate groups attached along the PAA chain can be designed and thus the extent of cross-linking can be controlled. Another example, methacryloyl chloride containing an acid chloride and a latent methacrylate group can be reacted with an amine group of chitosan through amide bond formation, converting the amine group to a methacrylate group. The methacrylate group can be crosslinker when exposed to UV radiation or an elevated temperature. As a result, a number of methacrylate groups attached along the chitosan backbone can be designed and thus the extent of cross-linking can be controlled.

As another example, methoxy-terminated poly(ethylene glycol) (mPEG) containing a terminal alcohol group can be reacted with a carboxylic acid group of poly(acrylic acid) to form an ester bond, attaching a mPEG onto PAA polymer. As a result, a number of mPEG groups attached along a polymer chain can be designed and controlled. mPEG-modified polymers such as PAA have several features.

Nanoparticles formed from mPEG-modified polymers can be stabilized by electrostatic interaction from carboxylic acid groups or steric repulsion from the PEG groups, or a combination of both. As another example, allyl, vinyl, styryl, acrylate and methacrylate groups can be conjugated to a polyelectrolyte to serve as polymerizable moieties. Examples of bifunctional molecules that are capable of reacting with carboxylic acid moieties in anionic polymers and that will leave polymerizable groups for cross-linking include, but are not limited to, 2-hydroxyethyl methacrylate ("HEMA"), 2-hydroxyethyl acrylate ("HEA"), N-(2-hydroxypropyl) methacrylamide, N-(2-aminopropyl) methacrylamide hydrochloride, N-(2-aminoethyl) methacrylamide hydrochloride, 2-aminoethyl methacrylate hydrochloride, allylamine, allyl alcohol, 1,1,1-trimethylolpropane monoallyl ether. Drug molecules, active ingredient compounds, or biomolecules can also be conjugated to a polyelectrolyte for target delivery. Fluorescent molecules can also be incorporated onto a polyelectrolyte to serve as fluorescent probes. Simple hydrophobic groups, such as short alkyl chains, can be attached to a polyelectrolyte to increase the pH sensitivity of the polymer or for other reasons. Complementary reactive groups can be also incorporated onto the same polymer chain or different polymer molecules to improve cross-linking. A combination of these molecules can be also incorporated onto the same polymer chain or different polymer molecules, with individual molecules serving different purposes. For example, a polymerizable group, HEMA, and active ingredient molecule can be modified to attach onto the same polymer chain, whereas the HEMA groups are used for cross-linking and active ingredients are used to enhance loading of active ingredient or to provide activity.

Conjugation can be performed before or after preparation of polymer nanoparticles.

Crosslinking

In certain embodiments, it is desired to crosslink the polymer particles of the present invention. Crosslinking can be induced by light, temperature, stoichiometric reagents, or the presence of a catalyst. Cross-linking may occur on surface layer or a specific location within the collapsed nanoparticles, or across the entire particle. Light-induced crosslinking can be triggered by UV and visible light of various wavelengths, in air or under an inert environment, with or without photoinitiators. Examples of photoinitiators that activate in the UV wavelength region include, but are not limited to, phenyl bis(2,4,6-trimethylbenzoyl)-phosphine oxide (IRGACURE 819, Ciba Corporation), acetophenone, and benzophenones such as 2-hydroxy-2-methylpropiophenone. Examples of photoinitiators that activate in the visible wavelength region include, but are not limited to, benzil and benzoin compounds, and camphorquinone. Cross-linking reaction can also be induced by the addition of an external crosslinker with or without the presence of a catalyst. Examples of external cross-linkers used to crosslink PAA, for example, include, but are not limited to, difunctional or polyfunctional alcohol (e.g. ethylene glycol, ethylenedioxy-bis(ethylamine), glycerol, polyethylene glycol), difunctional or polyfunctional amine (e.g, ethylene diamine, JEFFAMINE® polyetheramines (Huntsman), poly (ethyleneimine)). Catalysts are often required for this reaction. Such catalysts include, but are not limited to, carbodiimide compounds, e.g., N-(3-dimethylaminopropyl)-N'-ethylcarbodiimide hydrochloride) ("EDC"). Other examples of chemical cross-linkers include, but are not limited to, difunctional or polyfunctional aziridines (e.g., XAMA-7, Bayer MaterialScience LLC), difunctional or polyfunctional epoxy, or divalent or multivalent ions.

To enhance crosslinking reactions initiated by light or heat, polymerizable groups can be covalently attached along a polyelectrolyte chain. Methods of attaching the polymerizable groups to a polyelectrolyte chain are well known. Examples of such reactions include, but are not limited to e.g., esterification, amidation, addition, or condensation reactions. Examples of polymerizable groups include, but not limited to, allyl, vinyl, styryl, acrylate and methacrylate moiety. Examples of molecules that are capable of reacting with carboxylic acid moieties in anionic polymers and that will leave polymerizable groups for crosslinking include, but are not limited to, 2-hydroxyethyl methacrylate, 2-hydroxyethyl acrylate, N-(2-hydroxypropyl) methacrylamide, N-(2-aminopropyl) methacrylamide hydrochloride, N-(2-aminoethyl) methacrylamide hydrochloride, 2-aminoethyl methacrylate hydrochloride, allylamine, allyl alcohol, 1,1, 1-trimethylolpropane monoallyl ether.

In some embodiments, a polyelectrolyte incorporated with complementary reactive pairs is used. These reactive groups can be activated and controlled under specific conditions. After forming polymer particles, these reactive groups do not react until catalysts are added. A typical reaction between an azide and an alkyne group is known as "Click reaction", and a common catalyst system for this reaction is $Cu(SO_4)$/sodium ascorbate. In certain embodiments, this type of reaction can be used for chemical crosslinking.

In certain embodiments, a polyelectrolyte containing carboxylates or amines can be crosslinked via carbodiimide chemistry using an appropriate di-amine or dicarboxy functional crosslinker and an activating agent. Typical agents used to activate carboxy groups toward amide formation include, but are not limited to, N-Ethyl-N'-(3-dimethylaminopropyl)carbodiimide hydrochloride, Dicyclohexylcarbodiimide, N,N'-Diisopropylcarbodiimide. Di-amine functional crosslinkers include but are not limited to Ethylenediamine, O,O'-Bis(2-aminoethyl)octadecaethylene glycol, PEG-diamine, 1,3-diaminopropane, 2,2' (ethylenedioxy)bis(ethylamine), JEFFAMINE® polyetheramines (Huntsman), poly(ethyleneimine)).

Formation of Polymer Particles by Polymer Collapse

In various aspects, the present invention describes methods of producing polymer nanoparticles including active ingredients. In one embodiment, the polymer includes a polyelectrolyte and the nanoparticle is referred to as a polyelectrolyte nanoparticle. Polyelectrolyte nanoparticles including active ingredients can be produced in a variety of ways. As an example, the polyelectrolytes could be adsorbed to active ingredients using e.g. micelles, coacervation, or other similar formulation technologies to produce polyelectrolyte nanoparticles including active ingredients.

Figure 2:
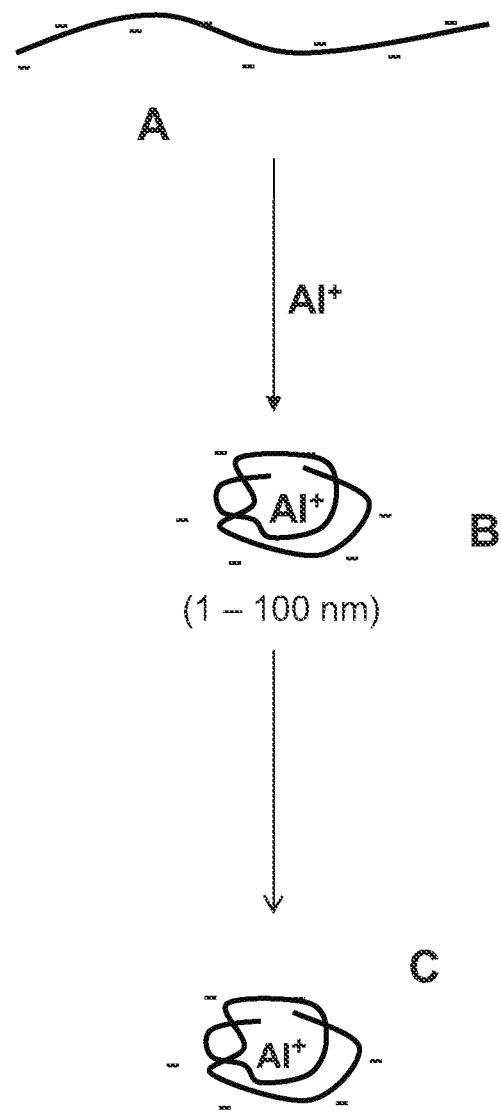
FIG. 2 is an exemplary illustration of direct collapse of polyelectrolyte around the active ingredient. A: Polyelectrolyte in an extended configuration. B: Addition of active ingredient and collapse of the polyelectrolyte around the active ingredient. C: Crosslinking

In various embodiments, the polyelectrolyte nanoparticles could also be produced using collapse of the polyelectrolyte around the active ingredient. This is shown in FIG. 2. For polyelectrolytes, at high charge density, e.g., when "monomer" units of the polymer are fully charged, an extended conformation is adopted due to electrostatic repulsion between similarly charged monomer units. Decreasing the charge density of the polymer by addition of salts can result in a transition of extended polymer chains to a more tightly-packed globular i.e. collapsed conformation. The collapse transition is driven by attractive interactions between the polymer segments that override the electrostatic repulsion forces at sufficiently small charge densities. If desired, in some embodiments, the collapsed conformation can be rendered permanent by crosslinking the polymer. In one embodiment, a polymer nanoparticle including active ingredients can be produced using a method including the steps of (a) dissolving a polyelectrolyte into an aqueous solution under solution conditions that render it charged and (b) adding an active ingredient that is oppositely charged under these conditions. If desired, the resulting polymer nanoparticle associated with active ingredient can be induced to form intra-particle crosslinks to stabilize the active ingredients associated with the nanoparticles. The extent of crosslinking can be used to control the release of active ingredients into the nanoparticles' environment. In some embodiments, water can be partially removed to afford a concentrated dispersion or completely removed to generate a dry solid. In some embodiments, a second solvent can be added to the resulting dispersion to precipitate the nanoparticles containing active ingredients. In some cases, the second solvent is a non-solvent for the nanoparticles.

It is also possible to produce polymer particles from a polyelectrolyte in other ways. In some embodiments, this includes the steps of (a) dissolving a polymer into aqueous solution, (b) associating an active ingredient with the polymer, and (c) causing the polymer to collapse. If desired, a metal ion or other species can be used instead of an active ingredient. As an example, if an active ingredient with an affinity for the polymer is added prior to collapse, the resulting material will be a polymer nanoparticle that includes an active ingredient. In further embodiments, water can be partially removed to afford a concentrated dispersion or completely removed to generate a dry solid. In further embodiments, a second solvent can be added to the resulting dispersion to precipitate the nanoparticles containing actives. In some embodiments, the second solvent is a non-solvent for the nanoparticles.

Potential affinities between the polymer and the species associated with the polymer may include any chemical groups that are found to have affinity for one another. These can include specific or non-specific interactions. Non-specific interactions include electrostatic interactions, hydrogen bonding, van der waals interactions, hydrophobic-hydrophobic associations, π-π stackings. Specific interactions can include nucleotide-nucleotide, antibody-antigen, biotinstreptavidin, or sugar-sugar interactions, where the polymer has the functionality of one half of the affinity pair and the species (e.g. active ingredient) associated with the polymer has the other half.

Potential methods to cause the polymer to collapse around the active ingredient associated or to be associated with the polymer (e.g., the active ingredient) can include decreasing the solubility of the polymer in the solvent. In some embodiments, this can be done by adding a non-solvent for the polymer. As an example, if the polymer is polyacrylic acid and the solvent is water, a high-salt ethanol solution can be added to cause the polymer to condense into a collapsed conformation and precipitate out of solution. The resulting product can be recovered and re-suspended into water. Other methods to cause the polymer to collapse include modification of the solubility by changing the temperature of the solution, e.g. for systems with low critical solution temperatures such as poly-(n-isopropylacrylamide) ("NIPAM"). If the polymer is a polyelectrolyte, the polymer can also be induced to collapse by addition of salt or modification of the pH after association between the active ingredient and the polymer has occurred.

In various embodiments, a similar process can be used for a hydrophobic active ingredient that can be dissolved to a limited extent in water at an elevated temperature but is relatively insoluble at room temperature. In one embodiment, the method includes the steps of (a) saturating an active ingredient in water at an elevated temperature in the presence of a polymer and a salt, (b) cooling the mixture. After cooling the mixture, the active ingredient will precipitate and the polymer will collapse around the active ingredient due to specific or non-specific interactions between active ingredient and the polymer. For example, poly(sodium sulfonate) and saturated chlorothalonil (a fungicide) in solution can be mixed at elevated temperature in the presence of NaCl. Upon cooling the mixture to lower temperature, both species precipitate, but poly(sodium sulfonate) can precipitate around chlorothalonil. If desired, the resulting polymer-encapsulated active ingredient nanoparticle can be induced to form intra-particle crosslinks to stabilize the active ingredients within the nanoparticles. The extent of crosslinking can be used to control the release of active ingredients into the nanoparticle's environment.

In some embodiments, an approach to produce polymer particles from a modified polyelectrolyte includes the steps of (a) conjugating hydrophobic groups along a polyelectrolyte chain, (b) dissolving the hydrophobically modified polyelectrolyte into an aqueous solution under solution conditions that render it charged, causing the hydrophobic groups to associate intramolecularly, and (c) crosslinking the polymer. When a polyelectrolyte is modified with hydrophobic groups, the collapse transition is driven by hydrophobic interactions in the absence of salt, as shown in FIG. 3.

Collapse can be monitored using, e.g., viscometry. Typically solutions of polymers show a viscosity higher than that of the solvent in which they are dissolved. For polyelectrolytes in particular, the pre-collapse polymeric solution can have a very high viscosity, with a syrupy consistency. After formation of polymer-encapsulated nanoparticles of active ingredients using collapse, a well-dispersed sample of the nanoparticles may show a much lower viscosity. This decreased viscosity after and even during collapse can be measured under appropriate conditions with either a vibrating viscometer or e.g. an Ostwald viscometer or other known methods in the art.

The formation of the nanoparticles can be demonstrated using dynamic light scattering (DLS), atomic force microscopy (AFM) or transmission electron microscopy (TEM). In DLS, formation of the nanoparticles is demonstrated by a decrease in average particle size relative to either the particle size of a solution of active ingredient of the same concentration or the particle size of a solution of the polymer encapsulant at the same concentration. In TEM or AFM the nanoparticles can be visualized directly.

If desired, the polymer nanoparticle can be induced to form intra or inter-particle crosslinks as described above. In certain embodiments, this crosslinking can be effected to stabilize the active ingredients or oppositely charged species associated with the polymer nanoparticle. The extent of crosslinking can be used to control the release of active ingredients or oppositely charged species into the nanoparticle's environment.

A redispersible solid prepared according to the present invention may be redispersed at a concentration higher than the solubility of the active ingredient under certain conditions. The redispersibility of the polymer-encapsulated nanoparticles may be determined by the solubility of the polymer encapsulant. As an example, if the polymer-encapsulant is highly water-soluble, nanoparticles of active ingredients encapsulated by that polymer will be able to be dispersed in water at high concentration, even if the active ingredient itself is not highly water soluble. This can be observed by a lack of precipitation of the active ingredient when redispersed above its solubility limit. This ability to redisperse at higher concentration may have applicability in a variety of formulations.

Formation of Polymer Particles from an Inorganic Metal Salt

In some embodiments, a polymer nanoparticles is formed without an associated active ingredient. The active ingredient is associated with the nanoparticle after the nanoparticle is fully formed. The association step may be accomplished in several different methods, each involving several different steps.

In one embodiment, the method of producing polymer nanoparticles includes the steps of (a) dissolving a polyelectrolyte into an aqueous solution under solution conditions that render it charged, (b) adding a species that is oppositely charged under these conditions, causing the polymer to collapse, (c) crosslinking, and (d) removing the oppositely charged species. A schematic describing one embodiment of this method is shown in FIG. 4. The resulting polymer nanoparticles can have a hollow structure, cavities, or can be a porous network structure. The polymer nanoparticles are capable of being loaded with active ingredients. In certain embodiments, the oppositely charged species is a metal ion e.g. from a metal salt. The resulting polymer nanoparticle can be crosslinked by any of the methods described above.

Examples of inorganic metal salts include, but are not limited to, the alkali and the alkaline earth metal salts like NaCl, KCl, KI, NaF, LiCl, LiBr, LiI, CsCl, CsI, $MgCl_2$, MgBr, $CaCl_2$. In certain embodiments the metal salt could be a nitrate, or a chloride salt of the transition metal series. Examples of transition metal salts are, but not limited to, $Zn(NO3)_2$, $ZnCl_2$, $FeCl_2$, $FeCl_3$, $Cu(NO_3)_2$. Other metal salts can be used as well like aluminum nitrate, bismuth nitrate, cerium nitrate, lead nitrate. In other embodiments, the salt can be the nitrate, chloride, iodide, bromide, or fluoride salt of ammonium.

Removal of the oppositely charged species can be accomplished by adjustment of pH. For example, if the polyelectrolyte has carboxylic acids as its ionizable groups, the oppositely charged species can be removed by acidification of the system by addition of a mineral or organic acid. This will displace the oppositely charged species and protonate the carboxylic acids. Similar methods can be used for ionizable species that are strong or weak acids or strong or weak bases.

Dialysis or similar membrane separation methods can be used to replace charged species with different charged species, which may be more amenable to exchange or loading of active ingredient. The extent of displacement will be dependent on the affinity between the oppositely charged species and the ionizable groups, and will also be dependent on the ease of ionization (e.g. the strength or weakness of the acid or base) of the ionizable group.

The extent of displacement will also be dependent on the pH that the solution is adjusted to. For example, if the polymer is a high molecular weight poly(acrylic acid), the oppositely charged species can be largely removed in water when the pH is of about 0.1 to about 3.5, in certain embodiments about 1.5 to about 2.0, and can also be removed by dialyzing against water at a similar pH value. In certain embodiments the oppositely charged species can be removed and replaced with a more benign charged species that does not prevent loading of the polymer particle with an active ingredient. As an example, if Fe(III) is used as the collapsing agent, dialysis against $Na^+$ can displace the Fe(III) and replace it with $Na^+$.

In some embodiments, the method to produce polymer nanoparticles includes the steps of (a) dissolving a polyelectrolyte into an aqueous solution under solution conditions that render it charged, (b) adding a species that is oppositely charged under these conditions, causing the polymer to collapse, (c) modifying the solution conditions to form an insoluble nanoparticle from the oppositely charged species, (d) crosslinking, and (e) modifying the solution conditions to remove the nanoparticles. In certain embodiments the nanoparticles are hydroxides, oxides, carbonates, or oxyhydroxides.

Figure 6:
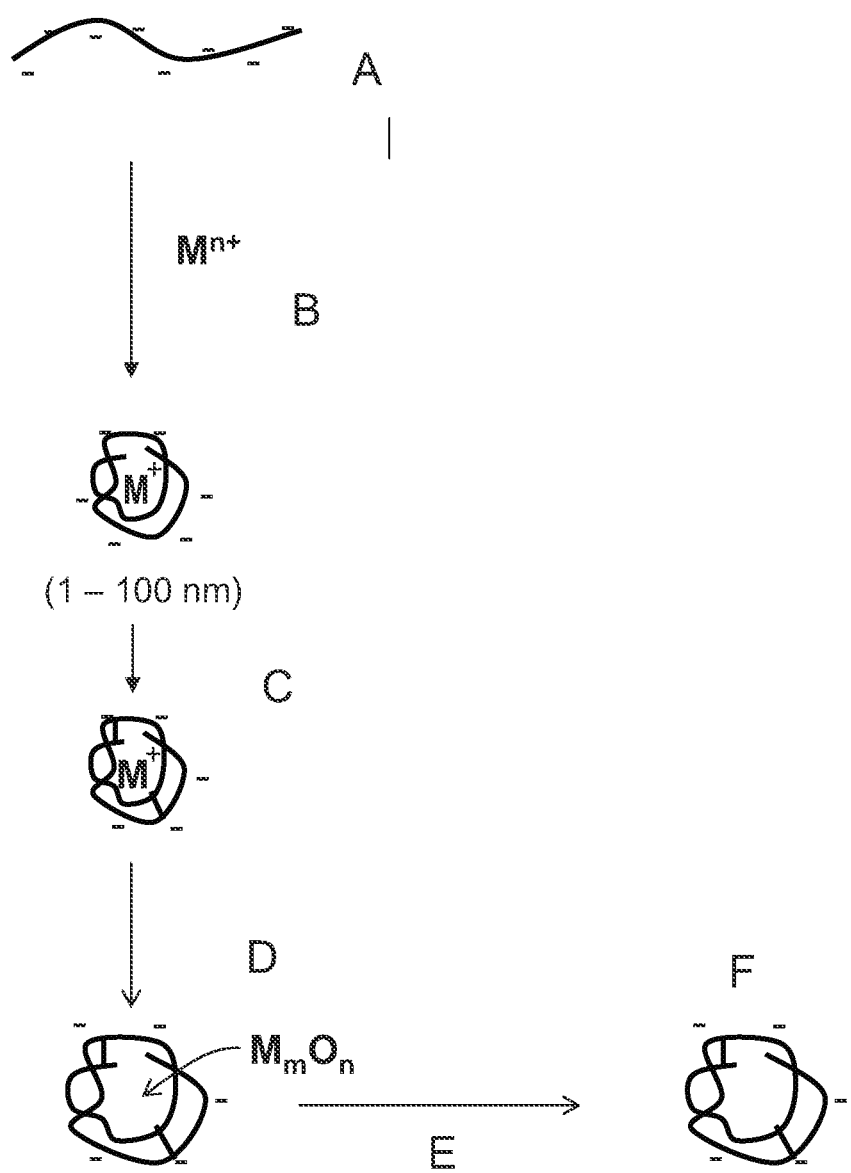
FIG. 6 illustrates the formation of polymer nanoparticle from metal hydroxide nanoparticles. A: Polyelectrolyte in an extended configuration. B: Collapsing polyelectrolye with metal oxide precursor ion. C: Crosslink collapsed polyelectrolyte. D: Formation of metal oxide. E: Removal of metal hydroxide. F: Polymer nanoparticle.

In certain embodiments, the oppositely charged species is a metal ion e.g. from a metal salt, and the hydroxide is a metal hydroxide, in which case step (c) can be accomplished through adjustment in pH. If the oppositely charged species is a metal ion, it can be converted to a hydroxide by adjustment of pH. The pH of the dispersion plays a critical role in converting metal ions to metal hydroxide. Metal ions can typically be converted to metal hydroxide by making the solution basic, with pH in the range of about 7 to about 14 (e.g, from about 7.5 to about 8.5; about 8.5 to about 10; about 10 to about 14. Conversion of the metal hydroxide to the metal oxide can be effected in a variety of ways, including heating to e.g. dehydrate the hydroxide, forming the oxide. If the dehydration is partial, a mixed oxide/hydroxide, referred to as an oxyhydroxide, can result. If the heating is performed in solution, the temperature can be in the range of 25-100° C.; 50-100° C.; or 70-90° C. In an some embodiments, the oxide can be formed from the hydroxide by recovering a dry solid from solution including the polymer particles and the hydroxide, and heating. The temperature of heating should be high enough to cause the hydroxide to convert to the oxide, without adversely effecting the polymer (e.g., decomposing the polymer). Temperature ranges will depend on the metal and the polymer, as well as the desired result. In some embodiments, the metal hydroxide, oxide, or oxyhydroxide can be formed by decomposition of a complex. As an example, Titanium(IV) bis(ammonium lactato)dihydroxide (TALH) can be used as a precursor for the formation of $TiO_2$ in aqueous solution. The decomposition of TALH under acidic (pH 3) or basic (pH 10) leads to the formation of $TiO_2$. An example illustrating the formation of polymer nanoparticles from metal oxide nanoparticles is shown in FIG. 6. If the insoluble nanoparticle is a carbonate, it can be formed by addition of a carbonate salt in step (c), and can be removed using similar techniques.

Step (e), removal of the nanoparticle, can be accomplished by adjustment of pH to conditions that would lead to the dissolution of the nanoparticle in solution. The pH of the dispersion also plays an important role in removing the nanoparticle. The metal hydroxyides typically dissolve in water with acidic pH, which can include pH in the range of about 0.1 to about 2.5; about 1.5 to about 2.0; about 1 to about 6; about 2 to about 5; or about 2 to about 4. The metal hydroxides can also be dissolved by dialyzing against water at a similar pH value. Oxides, oxyhydroxides, or carbonates can be removed in a similar fashion.

Formation of Polymer Particles Using Modified Polyelectrolytes

Figure 3:
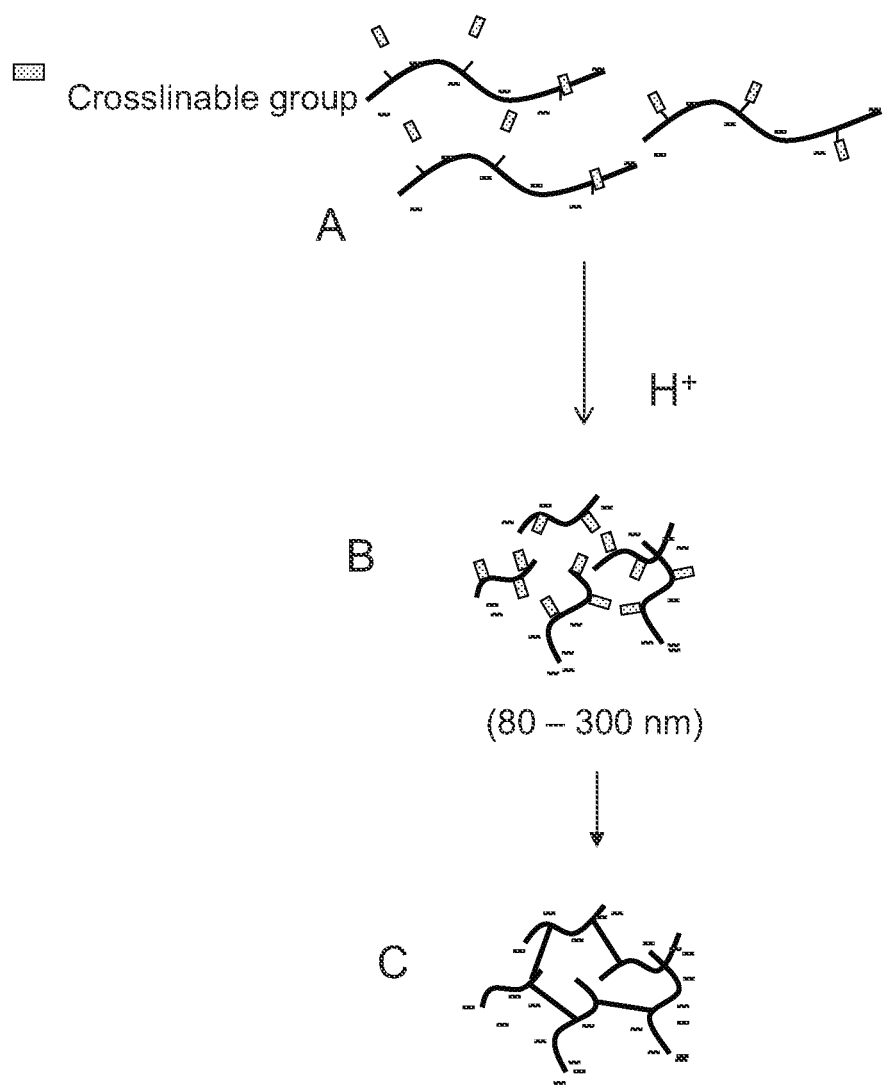
FIG. 3 illustrates formation of polymer nanoparticle from modified polyelectrolytes. A: Polyelectrolyte with hydrophobic groups in an extended configuration. B: collapse of modified polyelectrolytes C: Crosslinking
Figure 4:
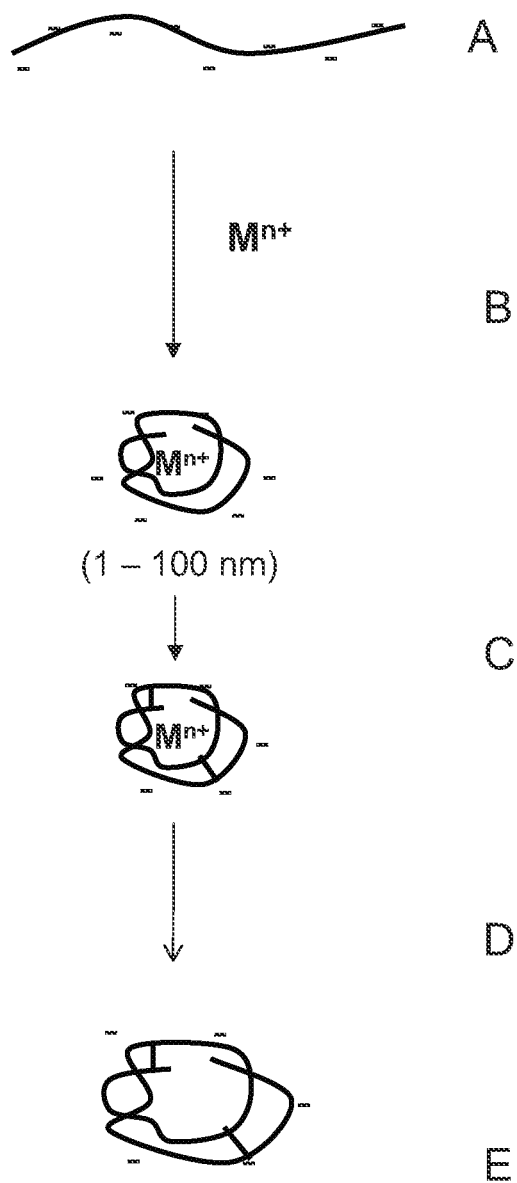
FIG. 4 illustrates formation of polymer nanoparticles from inorganic metal ion. A: polyelectrolyte in an extended configuration. B: Collapse of polyelectrolyte with metal salt. C: Crosslinking the collapsed polyelectrolyte. D: Removal of metal ion. E. Polymer nanoparticle.
Figure 5:
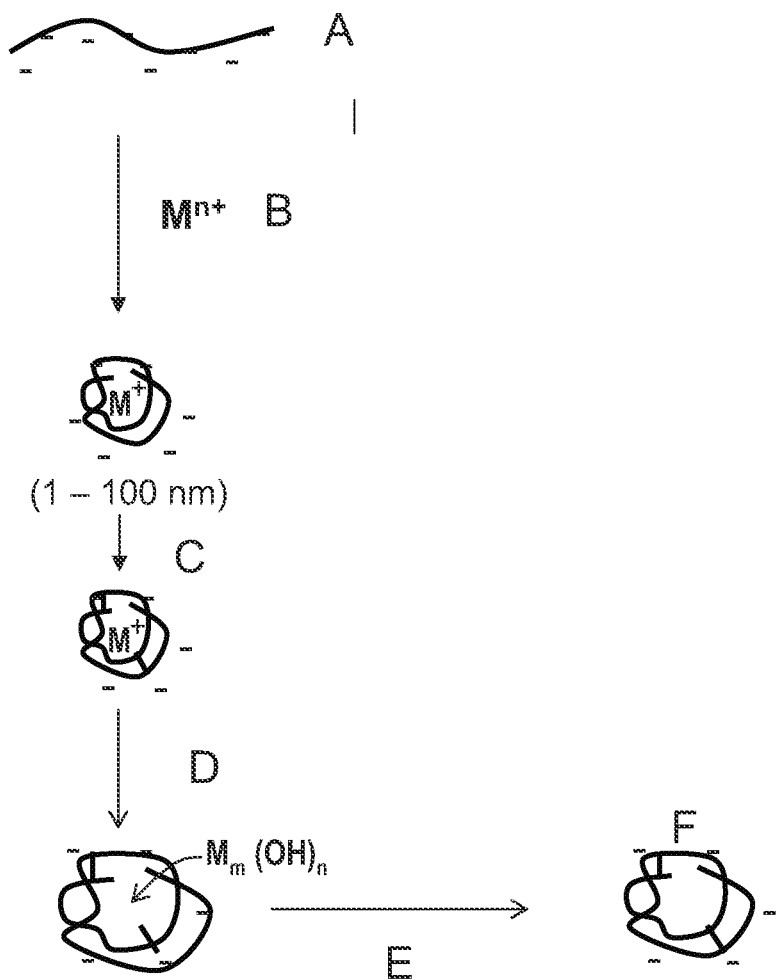
FIG. 5 illustrates the formation of polymer nanoparticle from metal hydroxide nanoparticles. A: Polyelectrolyte in an extended configuration. B: Collapsing polyelectrolye with metal hydroxide precursor ion. C. Crosslink collapsed polyelectrolyte. D: Formation of metal hydroxide. E: Removal of metal hydroxide. F: Polymer nanoparticle.

A modified polyelectrolyte can contain more than one type of functional group along the same polymer backbone, e.g., polymerizable groups (HEMA) and active ingredient molecules, or two functional groups of a reactive pair (alkyne and azide for Click reaction), as described above. In addition, a mixture of two polyelectrolytes, each containing one reactive group of a reactive pair, can also produce polymer particles, e.g. alkyne-modified PAA and azide-modified PAA. In one embodiment, modified polyelectrolytes can produce polymer particles. FIG. 3 illustrates steps to produce these particles. These steps involve (a) modifying PAA with, e.g., HEMA, according to procedure described previously, generating a pH-sensitive polymer, (b) dissolving the HEMA-modified PAA in water at pH>6, (c) lowering the pH (pH<6) of the solution and (d) cross-. The average size of polymer particles produced from this method ranges from 50 to 1000 nm. In some embodiments, particle size can be controlled by pH value. Large size occurred when pH value ranges from about 5 to about 6, and small size occurred when pH value ranges from about 3 to about 5.

Loading Active Ingredients

The polymer particles described in the present invention can be used to carry active ingredients. In one embodiment, a method to associate active ingredients with polymer particles includes the steps of (a) dissolving the active ingredients and the polyelectrolyte particles in a suitable solvent, (b) removing the solvent. The resulting polymer particles with associated active ingredients can be further processed by a method including the steps of (c) re-suspending the particles in a desired solvent under suitable conditions, and optionally (d) recovering dry particles containing active ingredients from the solvent. In some embodiments, there may be an addition of an agent that can promote the association between the active ingredient and the nanoparticle. This agent can be a cross-linking agent, a coordinating agent, or an agent that modifies the chemical functionality of either the active ingredient or the nanoparticle, including changes in pH that change the charge or protonation state of the active ingredient or the nanoparticle.

In certain embodiments, the suitable solvent of step (a) is an organic solvent in which both the polyelectrolyte particles and the active ingredient can be dissolved. Examples of suitable solvents include methanol, ethanol, and other polar hydrophilic solvents. In certain applications, where the active ingredient is desired to be suspended in water, the solvent in step (c) is an aqueous solvent or cosolvent. Suitable conditions for step (c) can include adjusting temperature, pH, ionic strength, or other solution conditions to effect re-suspending of the polymer particles with associated active ingredients.

For carboxy-based polymer particles containing active ingredients, the pH can be adjusted between about 7.1 to about 11, in some cases between about 7 to about 8. For other polyelectrolytes, suitable conditions to re-suspend them in aqueous solvents often include adjustment of pH such that enough of the ionizable groups on the polymers are ionized to allow them to re-suspend in the solvent. Step (d) is optionally used if the resulting particles need to be recovered as dry particles, this can be effected using freeze or spray drying, air drying, vacuum drying, or other approaches.

Polymer particles can be obtained from unmodified or modified polyelectrolytes, and prepared from the described procedures. They can contain metal ions, metal hydroxide or metal oxide. Their size can range from about 5 to about 300 nm. They can include only polymer particles with an empty interior, or can include cavities that may be dynamic. They can also be porous but not have discrete cavities. Alternately, they can be relatively densely packed but can be swollen or otherwise take up active ingredients.

In some embodiments, a different approach is used to associate polymer nanoparticles with active ingredients, including the steps of (a) dissolving the polymer nanoparticles in a suitable first solvent, (b) swelling the polymer nanoparticles by adding a second solvent containing active ingredient, (c) removing the second solvent. An alternative method includes the steps of (a) dissolving the polymer nanoparticles in a suitable first solvent, (b) swelling the polymer nanoparticles by adding a second solvent, (c) adding active ingredient, or alternatively adding additional second solvent that contains active ingredient, and (d) removing the second solvent. In certain embodiments, the first solvent can be hydrophilic and the second solvent can be more hydrophobic than the first solvent. In certain embodiments, the characteristics of the first solvent (temperature, pH, etc.) can be modified to make the polymer nanoparticles more or less hydrophilic or in a more extended or collapsed conformation. In certain embodiments, the first solvent can be aqueous. In certain embodiments, the pH of an aqueous solvent can be adjusted so that the polymer nanoparticles with ionizable groups are ionized. In certain embodiments, the pH of an aqueous solvent can be adjusted so that the polymer nanoparticles with ionizable groups are not ionized. As an example of this, a polymer nanoparticle with carboxy groups may be more susceptible to swelling under pH conditions that have the carboxy group in the acid form. In certain embodiments, the polymer nanoparticle can be dispersed in the first solvent or only partially soluble. In certain embodiments, the second solvent can be removed using evaporation, distillation, extraction, selective solvent removal, or dialysis. In certain embodiments, the second solvent has a vapor pressure higher than the first solvent. The amount of swelling of the polymer may be dependent on the type of polymer nanoparticle. For example, a hydrophilic polymer nanoparticle's tendency to swell may be dependent on the characteristics of the second solvent. In certain embodiments, a hydrophilic polymer nanoparticle will be more swellable by a polar second solvent. In certain embodiments, a hydrophobic polymer nanoparticle will be more swellable by a hydrophobic solvent. It is also possible to enhance swelling by including chemical groups in the solvent and polymer nanoparticle that have an affinity for one another, e.g. carboxy and amine, acid and base, etc. Swelling of the polymer nanoparticles can be observed by changes in size of the particles as measured by light scattering, chromatography, cryogentic transmission electron microscopy, solution-based atomic force microscopy. Alternately, swelling of the polymer nanoparticles by an immiscible second solvent can be observed by disappearance of an observable second solvent phase due to partitioning of the solvent into the polymer nanoparticles. Swelling can also be observed by changes in viscosity. Swelling can also be observed by spectroscopy. As an exemplary embodiment, if the solvent carrying active ingredients imparts a spectral signature to the active ingredients, and that spectral signature is modified on incorporation with the polymer nanoparticle, this can demonstrate swelling and incorporation of the active ingredient. A molecule showing these characteristics is pyrene, which changes its emission characteristics depending on the hydrophobicity or hydrophilicity of its microenvironment.

Examples of suitable second organic solvents include, but are not limited to, methanol, ethanol, ethyl acetate, isopropanol, methoxy propanol, butanol, DMSO, dioxane, DMF, NMP, THF, acetone, dichloromethane, toluene, or a mixture of two or more of the solvents. Some of these solvents can be removed by evaporation. In some embodiments, the first solvent is miscible in the second solvent. In some embodiments, the first solvent and second solvent are partially miscible. In some embodiments, the first solvent and second solvent are immiscible.

In some embodiments, a different approach is used to associate polymer nanoparticles with active ingredients, including the steps of (a) dissolving the polymer nanoparticles and active ingredient in a suitable first solvent, (b) adding second solvent, (c) removing first solvent.

Examples of suitable first solvents include, but are not limited to, methanol, ethanol, isopropanol, methoxy propanol, butanol, DMSO, dioxane, DMF, NMP, THF, acetone, or a mixture of two or more of the solvents. These solvents can be removed by evaporation. In these embodiments, the second solvent is miscible in the first solvent, but poor solvent to active ingredients. The second solvent can be aqueous.

Figure 7:
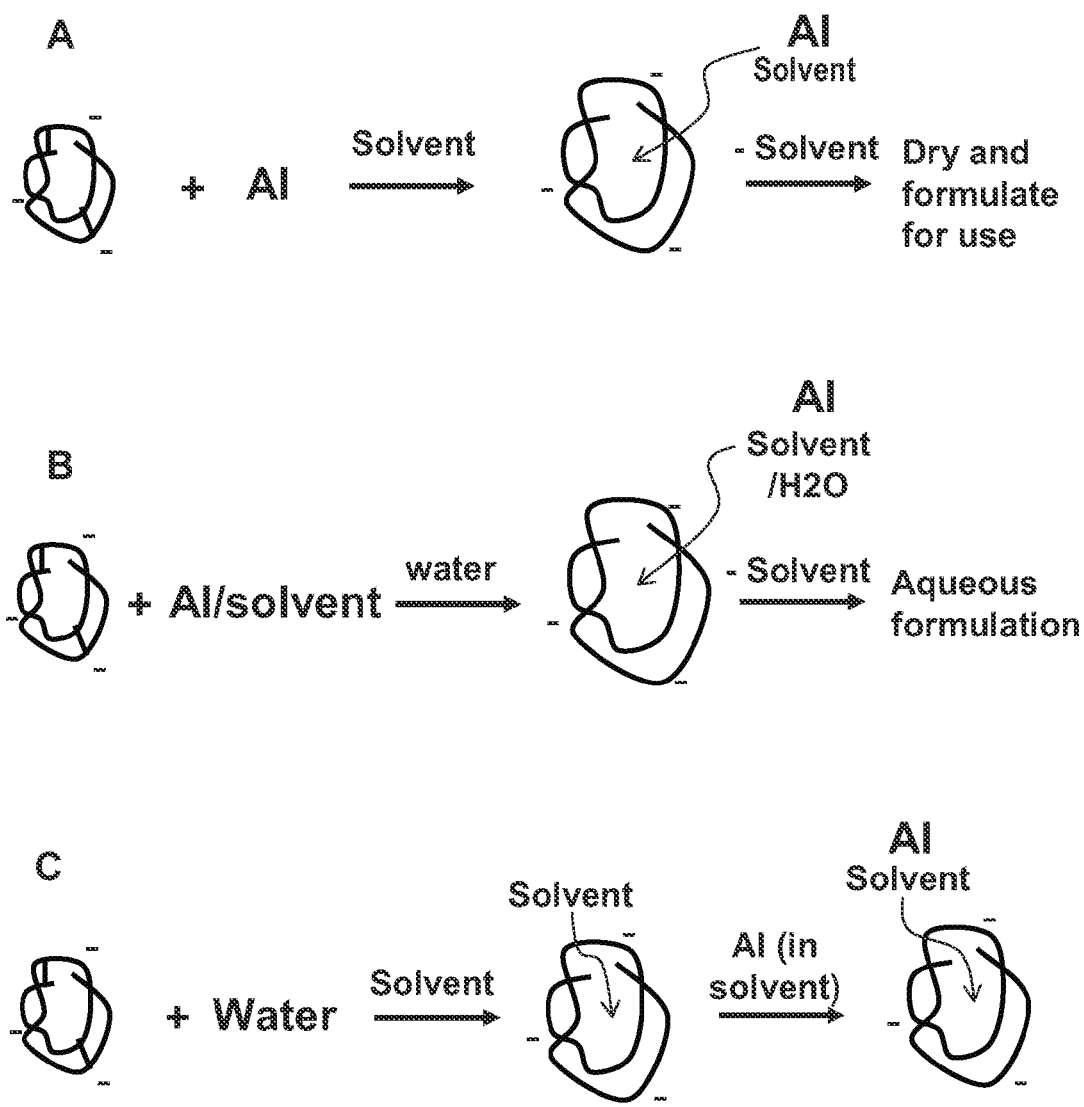
FIG. 7 illustrates methods of active ingredients loading into hollow nanoparticles. A: Use appropriate solvent to swell nanocapsules in presence of AI. B: Use miscible solvent system to partition AI into nanocapsules. C: Use immiscible solvent to swell nanocapsules in presence of AI.

The active ingredients associated with the polymer nanoparticles can be dispersed throughout the polymer nanoparticle. They can also be enriched in regions of the polymer nanoparticle, either being predominantly on the surface of the polymer nanoparticle or predominantly contained within the polymer nanoparticle. If the polymer nanoparticle has one or more discrete cavities, the active ingredient can be contained within the cavities. A diagram illustrating the different methods used to load active ingredients is shown in FIG. 7.

Formation of Surface-Active Agents of Active Ingredients

In various aspects, the present invention also provides methods of producing a surface-active agent of an active ingredient (e.g., surface-active, active ingredient). These surface-active active ingredients can be produced in a variety of means. In one embodiment, this would include the steps of (a) mixing a water-insoluble active ingredient containing a functional group with a water-soluble reagent containing a complementary reactive group (b) allowing the reaction to proceed to completion at room temperature or an elevated temperature with removal of side products if necessary, and optionally (c) removing the organic solvent if applied. If desired, a catalyst for the reaction can be used.

Under certain conditions, the surface-active agent of an active ingredient has active properties as produced. Under other conditions, the surface-active agent of an active ingredient is only activated when there is a change in solution conditions, such as, e.g., pH, that can cause liberation of the active ingredient from the surface-active agent of the active ingredient.

The surface active agents of active ingredients can provide many functions. They can help increase the amount of active ingredient that can be loaded into a given formulation. They can also add stability to a given formulation due to their surface active agent characteristic. They can also be used as precursors or monomers to produce polymer particles that are loaded with active ingredients. They can also be used to load multiple active ingredients in a formulation, where one or both of the active ingredients are provided as a surface-active, active ingredient.

In various aspects, the present invention provides methods of producing a surface-active agent of active ingredient. These surface-active active ingredients can be produced in a variety of means, including chemical reaction between a water-soluble reagent and the water-insoluble active ingredient. In various embodiments, a chemical reaction between a functional group of a water-insoluble active ingredient with a complimentary group of a water-soluble agent may be used. In various embodiments, the chemical reaction may be, but not limited to, esterification.

An esterification reaction joins an alcohol group with a carboxylic acid groups, forming an ester bond. The esterification reaction conditions can be at room temperature or an elevated temperature, in the presence or absence of organic solvents, in the presence or absence of a catalyst. In one embodiment, an esterification reaction can occur between a water-insoluble active ingredient containing a carboxylic acid moiety and a water-soluble agent containing an alcohol moiety. Reversibly, an esterification reaction can occur between a water-soluble active ingredient containing a carboxylic acid moiety and a water-insoluble agent containing an alcohol moiety would also work.

Suitable active ingredients containing carboxylic acid group include but are not limited to herbicidal acid groups including benzoic acids, aryloxyphenoxypropionic acids, phenoxyacetic acids, phenoxypropionic acids, phenoxybutyric acids, picolinic acids, and quinolones drugs, and also include but are not limited to, cinoxacin, nalidixic acid, pipemidic acid, ofloxacin, levofloxacin, sparfloxacin, tosufloxacin, clinafloxacin, gemifloxacin, moxifloxacin, gatifloxacin.

Suitable water-soluble agents include, but are not limited to suitably terminated poly(ethylene glycol) or poly(propylene glycol). In one embodiment, the esterification reaction occurred between the carboxylic acid of 2,4-dichlorophenoxyacetic acid ("2,4-D") with the terminal alcohol group of methoxy-terminated poly(ethylene glycol), joining the hydrophobic 2,4-D molecule with the hydrophilic poly (ethylene glycol) through an ester bond formation, generating a surface-active agent of 2,4-D. In one embodiment, the esterification reaction was performed in toluene at reflux temperature in the presence of concentrated $H_2SO_4$. In one embodiment, the esterification reaction was performed under silica gel catalyst at 150° C. in the absence of an organic solvent.

Combination of Surface-Active Agents of Active Ingredients and Polymer Nanoparticles Including Active Ingredients In various aspects, the surface-active active ingredient and the polymer-nanoparticles including active ingredient can be used together to produce nanoparticles with increased loading of active ingredients and that are more stable as a dispersion. The surface-active active ingredients could be adsorbed onto nanoparticles. In various embodiments, this may include the steps of (a) synthesizing surface-active active ingredients, (b) preparing polymer nanoparticles including active ingredients according to the present invention, (c) mixing the surface-active ingredients and a dispersion of polymer nanoparticles including active ingredients. Step (c) can be conducted in a variety of ways. Surface-active ingredients can be added directly to the nanoparticle dispersion. In various embodiments, surface-active ingredients are first dissolved in water with a pH similar to that of the nanoparticle dispersions, and then added to the nanoparticle dispersion. In some embodiments, the reverse order of addition can be performed. In some embodiments, the pH of the dispersion and active ingredient solution may be between 5 and 9. The amount of surface-active ingredient that is added may be below the necessary concentration to form separate micelles of surface-active ingredient that are not bound to the nanoparticles. In various embodiments, the surface-active ingredient can be added neat to the nanoparticle dispersion. In some embodiments, the surface-active ingredient can be added during the preparation of polymer nanoparticles including active ingredient.

Polymers Formed from Active Ingredients

In various aspects, the present invention provides methods of producing aqueous polymer solutions containing nanostructures including active ingredients. Aqueous polymer solutions containing nanostructures including active ingredients can be produced in a variety of ways. Examples include, but are not limited to, grafting an active ingredient onto an existing water-soluble monomer, and copolymerizing randomly or controllably monomer containing active ingredient with monomer containing water-soluble moiety. In one embodiment, grafting an active ingredient onto an existing polymer would include the steps of (a) grafting an active ingredient onto an existing water-soluble polymer, and (b) dissolving the grafted polymers in a solvent. In some embodiments, this would include the steps of (a) functionalizing the active ingredients, (b) grafting the active ingredients onto an existing water-soluble polymer, and (c) dissolving the grafted polymers in a solvent. In certain embodiments, the polymer is a polyelectrolyte which may or may not be capable of collapse.

The driving force behind the formation of nanostructures can be caused by one or more of: hydrogen bonding between water molecules being interrupted by the grafted active ingredient; and/or the associative interaction among active ingredient groups. At a low polymer concentration, intramolecular interactions among active ingredient groups grafted on the same polymer chain can cause the polymer to collapse, forming nanoparticles. As the polymer concentration increases, intermolecular interactions of active ingredient groups from one collapsed polymer to an adjacent one can begin, bridging between two collapsed polymers. As polymer concentrations further increase, the polymer chains can move closer to one another, and thus intermolecular interactions of active ingredient from one polymer chain to the adjacent one will dominate.

In some embodiments, nanoparticles can be formed by causing the polymer to collapse using the techniques described previously. In some embodiments, the polymer can include an uncharged polymer capable of collapse such as poly-(n-isopropylacrylamide) (NIPAM). The associative interaction among active ingredient groups can be intra- or intermolecular or a combination of both depending on concentrations of the polymers.

In some embodiments, grafting an active ingredient onto an existing polymer would include the steps of (a) functionalizing an active ingredient, i.e. monoesterification of 2,4-D with ethylene glycol, attaching a 2,4-D molecule to one end of a diol molecule, (b) grafting the synthesized active ingredient containing an alcohol group onto a carboxy-containing polymer via esterification reaction, and (c) dissolving the AI-graft polymers in water, forming nanostructures containing active ingredients.

In various embodiments, aqueous polymer solutions containing nanostructures including active ingredients can be produced by copolymerizing monomers containing active ingredient with monomers containing water-soluble moieties. Examples of monomers containing water-soluble moieties include, but are not limited to, N-isopropyl acrylamide (NIPAM), acrylate-terminated PEG, acrylic acid, methacrylic acid, 2-hydroxyethyl methacrylate, styrene sulfonate, vinyl pyridine, allylamine, N,N-dimethylaminoethyl acrylate, N,N-dimethylaminoethyl methacrylate.

In some embodiments, an aqueous solution of random copolymer containing active ingredient could be produced using a process including the steps of (a) synthesizing a monomer containing active ingredient, (b) copolymerizing the synthesized monomer with a monomer or mixture of monomers containing water-soluble moiety, and (c) dissolving the copolymer in water. Copolymerization conditions in Step (b) can be in an organic solvent at an elevated temperature in the presence of an initiator. In some embodiments, an aqueous solution of random copolymer containing active ingredient could be produced using a process including the steps of (a) synthesizing a monomer containing active ingredient, (b) emulsion copolymerizing the monomer containing active ingredient with NIPAM at temperature above the low critical solution temperature of poly (NIPAM), forming copolymer particles containing active ingredient, (c) cooling the temperature of the reaction to room temperature. After cooling, the micron-scale polymer-active ingredient particles disintegrate, the copolymers dissolve in water, and active ingredients on the same or adjacent polymers associate to form nanostructures.

In some embodiments, an aqueous solution of random copolymer containing active ingredient could be produced using a process comprising the steps of (a) synthesizing a monomer containing active ingredient, (b) emulsion copolymerizing the monomer containing active ingredient with methacrylic acid or acrylic acid at low pH, forming copolymer particles containing active ingredient, (c) and ionizing the carboxylic acid groups. Step (c) can alternately or additionally include cooling the system. The cooling or ionization steps causes the micro-scale polymer-active ingredient particles to disintegrate, the copolymers to dissolve in water, and active ingredients on the same or adjacent polymer chains to associate to form nanostructures.

In some embodiments, an aqueous solution of block copolymer containing active ingredient could be produced using a process including the steps of (a) synthesizing a monomer containing active ingredient, (b) adding a water-soluble macroinitiator, (c) polymerization of the synthesized monomer using the water-soluble macroinitiator, forming a block copolymer including one hydrophilic and one hydrophobic block. In an aqueous solution, the hydrophobic block of individual copolymers can associate, forming nanostructures including active ingredients.

The Use of Surface-Active Agents of Active Ingredients in Producing Polymer Particles In various aspects, the surface-active agent of active ingredients may be used to increase active ingredients loading in the polymer solution containing nanostructures of active ingredient. Alternatively, the surface-active agent of active ingredients may be used to decrease the mean polymer diameter during the preparation of polymer particles. Ultimately, the surface-active agent of active ingredients may be used to reduce viscosity of the polymer solution.

In one embodiment, this would include the steps of (a) synthesizing a monomer containing active ingredients, (b) synthesizing surface-active agent of active ingredient, (b) copolymerizing the monomer containing active ingredients with monomer containing ionic groups. The copolymerization can be an emulsion polymerization. In certain embodiments, the copolymerization can be an emulsion polymerization in water at low pH. The resulting polymer particles can then be ionized and dispersed in water, yielding an aqueous polymer solution with polymer particles including nanostructures including active ingredients associated on the same or adjacent polymers.

EXAMPLES

Particle size and size distribution were measured using dynamic light scattering (DLS). The particle size was reported from at least an average of 25 measurements, and shown in volume percentage.

Viscosity was measured using Oswald viscometer at 21° C. Viscosity of individual solution or dispersion was reported in time, which took the solution or dispersion traveled between two marks on the viscometer.

UV lamps were at 254 nm.

Note that the nomenclature $M_xN_y$/PAA refers to a $M_xN_y$ nanoparticle associated with poly(acrylic acid). The $M_xN_y$ can also be an ion e.g. $Zn^{2+}$/PAA, in which case it refers to a poly(acrylic acid) nanoparticle containing $Zn^{2+}$.

A. Formation of Polymer Nanoparticles Using a Combination of a Common Salt (NaCl) and UV Treatment:

Example 1: Production of Polymer Nanoparticles by Treating Poly(Acrylic Acid) (PAA) Solution with NaCl In a 250 mL beaker equipped with a magnetic stir bar, solid PAA (0.100 g, Mw=450,000 Dalton) and deionized water (100 g) were weighed. The solution was magnetically stirred until PAA completely dissolved, then the pH was adjusted to 9.63 using aqueous 1N NaOH.

To a separate beaker equipped with a magnetic stir bar, 50 g of the aqueous solution of PAA (0.1 wt %) was transferred. While stirring, 5 mL of 3M NaCl was added dropwise. The solution remained transparent.

To two separate beakers equipped each with magnetic bars, 25 g aqueous PAA solution and 25 g aqueous PAA solution with NaCl were transferred. While stirring, the solutions were exposed to UV lamps for 5 min.

TABLE 1

Summary results of viscosity and DLS measurements of PAA solution in the presence and absence of NaCl, with and without UV treatment.

|   | Viscosity (second) | DLS |
|---|---|---|
| PAA solution before UV treatment | 681 | N/A |
| PAA solution after UV treatment | 468 | N/A |
| PAA solution + NaCl before UV treatment | 101 | 24 nm (99%) |
| PAA solution + NaCl after UV treatment | 100 | 37 nm (13%) 10 nm (87%) |
| Deionized water | 71 | N/A |

TABLE 2

Summary results of viscosity and DLS measurements of HEMA-modified PAA solution in the presence and absence of NaCl, with and without UV treatment.

|   | Viscosity (cP) | DLS |
|---|---|---|
| HEMA-modified PAA solution before NaCl/UV treatment | 4.8 | N/A |
| HEMA-modified PAA + NaCl before UV treatment | 1.2 | 28 (22%) |
|  | 1.0 | 7 (78%) |
| HEMA-modified PAA + NaCl after UV treatment |  | 24 (23%) 5 (77%) |

Example 2: Production of Polymer Nanoparticles by Treating HEMA-Modified PAA Solution with NaCl Synthesis of HEMA-Modified PAA (Low Degree of HEMA Grafting):

To a 250 mL round bottom flask, solid PAA (3.0 g, Mw=450,000 Dalton) and liquid DMSO (100 g) were transferred. The flask was magnetically stirred until PAA completely dissolved. Solid 4-(dimethylamino)pyridine (DMAP, 0.34 g) and liquid 2-hydroxyethyl methacrylate (HEMA, 10.8 g) were transferred to the reaction flask. The reaction mixture was stirred until all DMAP was completely dissolved, then solid N-(3-Dimethylaminopropyl)-N'-ethylcarbodiimide hydrochloride (EDC, 0.53 g) was transferred. The reaction mixture was stirred at room temperature for 16 hours. After 16 hours, the mixture was added dropwise into a 1 L beaker containing 700 mL 2-propanol, yielding a precipitate. The supernatant was discarded, and the precipitate was washed twice with 2-propanol (100 mL each). Removing residual 2-propanol under vacuum overnight yielded solid HEMA-modified PAA.

Preparation of Aqueous HEMA-Modified PAA Solution (0.83 wt %):

In a 100 mL beaker equipped with a magnetic stir bar, solid HEMA-modified PAA (0.332 g, Mw=450,000 Dalton) and deionized water (40 g) were weighed. While the mixture was stirring, the pH of the solution was kept constant around 8.0 by adding 1N NaOH solution. Basic pH would more quickly dissolve solid HEMA-modified PAA. After the solid polymer was completely dissolved, the solution was transparent and the pH of the solution was measured at 7.9.

PAA powder (16.6 mg, Mw=1800 D) and 133 mL DI water were added to above HEMA-modified PAA solution and stirred until the solution was transparent. The pH was 7.3. NaCl solution (12.4 mL, 3M) was slowly added while being stirred by a magnetic stir bar. Then 2-hydroxy-2-methyl-propiophenone (1.8 mg, 97%) was added and stirred for 3 h. The solution was UV-irradiated for 1 hour. The solutions, before and after UV-irradiation, were characterized by viscosity and particle size which were shown in Table 2.

The pH of above solution was then adjusted to 2, polymer particles were precipitated out of the solution. The precipitate was rinsed by DI water of pH 2 and centrifuged to remove supernatant. This was repeated for three times, and finally the precipitate was dissolved in water and pH was adjusted to 6.5.

B. Formation of Polymer Nanoparticles with Hollow Structure and Cavities Using an Inorganic Metal Salt and Crosslinking Followed by Etching the Resulting Metal Oxide/Hydroxide:

Example 3: Production of Polymer Nanoparticles with Hollow Structure and Cavities by Treating Poly(Acrylic Acid) Solution with $Al(NO_3)_3$ (FIG. 1)

Preparation of Aluminum Hydroxide-Encapsulated PAA Nanoparticles:

$Al(NO_3)_3$ aq. solution (25 mM, 300 mL) was loaded in a 1 L beaker (A) equipped with a magnetic stirrer, NaOH aq solution (100 mM, 145 mL) was added slowly into the beaker by a feeding pump. Another 1 L beaker (B) was charged with polyacrylic acid aqueous solution (Mw=450 KD, pH 7, 4 mg/mL, 300 mL) and stirred by a magnetic stirrer. The solution from the beaker (A) was slowly added into the beaker (B) by a feeding pump over 3 hours, meanwhile the pH of the solution in the beaker (B) was maintained to 7 by continuously adding NaOH aq solution (100 mM). The obtained solution was UV irradiated under an UV lamp (252 nm) for 2 hours under stirring condition. The solution was sonicated for 10 min by using a VirSonic sonicator (at power of 50%), and then was adjusted to pH 8.5 by adding NaOH aq solution (100 mM). The above solution was concentrated 10 times by a rotary evaporator ("rotovap"). The formed PAA-encapsulated $Al(OH)_3$ particles were precipitated out by adding NaCl/ethanol solution. The precipitate was centrifuged and rinsed 3 times by 70% ethanol. The precipitate was re-suspended in DI water and freeze-dried to obtain a dry powder. The PAA-encapsulated $Al(OH)_3$ particles were characterized by DLS and the average size was determined to be 20 nm.

Crosslinking Reaction by EDC:

$PAA/Al(OH)_3$ aq solution (5 mg/mL, 500 mL) was loaded in a 2 L beaker equipped with a magnetic stirrer. A solution of 2, 2'-(ethylenedioxy)bis(ethylamine) (2.5 mmol, 0.3705 g in 50 mL DI water) was slowly added at 0.5 mL/min feeding rate to above stirred solution. The solution was allowed to stir for another 2 hours at room temperature. Then to this mixture was added slowly a solution of 1-Ethyl-3-[3-dimethylaminopropyl]carbodiimide hydrochloride (0.985 g in 500 mL DI water) over 12 hours. The reaction mixture was allowed to stir overnight. The crosslinked polymer/inorganic particles were precipitated out by adding NaCl/ethanol solution. The precipitate was centrifuged out and rinsed 3 times by 70% ethanol. The precipitate was re-suspended in DI water.

Removal of Aluminum Hydroxide Particles:

To a stirred aqueous solution of the crosslinked polymer/inorganic particle (15 mg/mL), was added HCl solution (2 N) until the pH reached 1.5. The obtained transparent solution was transferred into a dialysis tubing (Spectra/Por dialysis membrane, MWCO 12-14,000), and dialyzed against DI water at pH of 1.5 for 3 days with 3 water changes per day. The dialyzed solution was adjusted to pH of 8.5 by adding NaOH (0.5 N), and then dialyzed against DI water for one day with 3 water changes. The obtained solution was freeze-dried to obtain dry powder of polymer capsules. The polymer capsules were characterized by DLS, and the average size was determined to be 20 nm.

Figure 10:
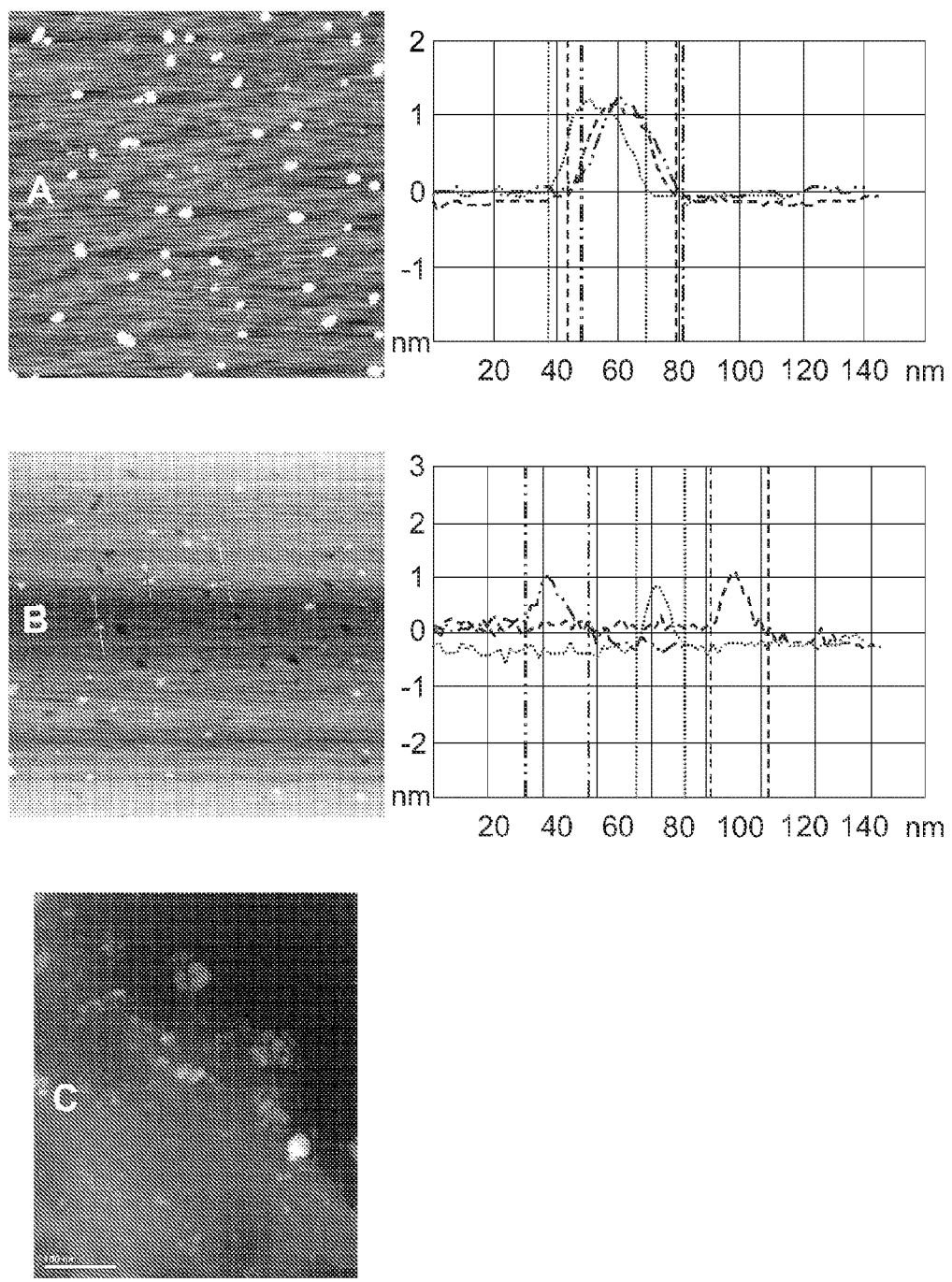
FIG. 10: Atomic force microscopy (A, B) and transmission electron microscopy (TEM) (C) images of polyelectrolyte particles (A) containing aluminum hydroxide and (B, C) after aluminum hydroxide has been removed.

FIG. 10 shows AFM images of (A) a PAA polymer particle including aluminum hydroxide nanoparticles, and (B) the polymer particles of (A) after aluminum hydroxide has been removed. The PAA containing aluminum hydroxide particles appeared to be larger and harder than those after aluminum hydroxide particles were removed. FIG. 10 C also shows TEM image of the PAA particles after removing aluminum hydroxide particles.

C. Formation of Polymer Particles by a Combination of Acidification and UV/Visible Light Treatment:

Example 4: Production of Polymer Particles by Treating HEMA-Modified Poly(Acrylic Acid) with Acid Synthesis of HEMA-Modified PAA (High Degree of HEMA Grafting):

To a 250 mL round bottom flask, solid PAA (2.0 g, Mw=450,000 Dalton) and liquid DMSO (100 g) were added. The flask was magnetically stirred until PAA completely dissolved. Solid 4-(dimethylamino)pyridine (DMAP, 0.34 g) and liquid 2-hydroxyethyl methacrylate (HEMA, 21.7 g) were added to the reaction flask. The reaction mixture was stirred until all DMAP was completely dissolved, then solid N-(3-Dimethylaminopropyl)-N'-ethylcarbodiimide hydrochloride (EDC, 2.67 g) was added. The reaction mixture was stirred at room temperature for 16 hours. After 16 hours, the mixture was added dropwise into a 1 L beaker containing 900 mL deionized water, yielding a precipitate. The supernatant was discarded, and the precipitate was washed twice with deionized water (500 mL each). The precipitate was redissolved in deionized water (400 mL) with the aid of standard 0.100N NaOH (118 mL) which resulted the transparent solution with solids content of 0.73 wt % and pH of 9.75. From these results, the extent of HEMA grafting was calculated and obtained a value of 27 mol %.

Preparation of Aqueous HEMA-Modified PAA Solution (0.2 wt %):

In a 250 mL beaker equipped with a magnetic stir bar, 27.4 g of HEMA-modified PAA solution (0.73 wt %) and deionized water (72.6 g) were weighed. The resulting mixture appeared transparent and had a pH of 8.90. While the mixture was stirring, aqueous HCl (0.1N) was added dropwise. The transparent solution became translucent at pH of around 6.5 and then opaque at 6.03. The opaque nature indicated that polymer particles of large size were forming. The polymer particles were characterized by DLS, and the average size was determined to be 211 nm (100% volume intensity).

Crosslinking of HEMA-Modified PAA Particles by UV and Visible Light:

A portion (5 mL) of the opaque mixture was transferred to 4 vials. To one vial was added a tiny amount of a UV photoinitiator (2-hydroxy-2-methylpropiophenone, HMPP, 0.00088 g). Visible light photoinitiators, Benzil (0.00137 g) and camphorquinone (0.0021 g) were added to the second and third vial. The fourth vial did not contain any photoinitiator. All 4 vials were capped, wrapped in an aluminum foil, and stirred at room temperature over 16 hours. The vial not having a photoinitiator and the vial containing the UV photoinitiator were uncapped and exposed to UV lamp for 5 minutes. The other two vials were purged with nitrogen gas for 5 minutes and exposed to sun lamp for 10 minutes.

TABLE 3

Summary results of DLS measurements of polymer particles after exposed to radiation

| | control | no initiator (UV) | HMPP (UV) | Benzil (visible) | Camphorquinone (visible) |
|---|---|---|---|---|---|
| pH 6.03 | 211 nm (100%) | 269 nm (100%) | 194 nm (100%) | 330 nm (100%) | 210 nm (100%) |
| adjusted to pH 10 | N/A | N/A | 203 nm (100%) | 372 nm (100%) | 313 nm (100%) |

Example 5: Production of Polymer Particles by Treating a Mixture of Azide-Modified PAA and Alkyne-Modified PAA with Acid Synthesis of 3-azidopropanol:

In a 100 mL round bottom flask, liquid 3-chloropropanol (10.0 g, 1.0 equiv), solid sodium azide (17.19 g, 2.5 equiv) were reacted in DMF for 40 hours at 100° C. The reaction mixture was cooled to room temperature, poured into a reparatory funnel and extracted with diethyl ether (300 mL) and brine solution (500 mL). The organic layer was separated and dried over $MgSO_4$. Rotary evaporation removed the diethyl ether solvent at room temperature and yielded crude 3-azidopropanol (12.5 g). $^1$H-NMR (δ, ppm) $CDCl_3$: 3.76-3.73 (t, 2H, HOC$\underline{H}_2$CH$_2$CH$_2$N$_3$), 3.46-3.43 (t, 2H, HOCH$_2$CH$_2$C$\underline{H}_2$N$_3$), 2.09 (br-s, 1H, OH), 1.86-1.80 (m, 2H, HOCH$_2$C$\underline{H}_2$CH$_2$N$_3$). IR neat (cm$^{-1}$): 2100 (N=N=N).

Synthesis of $N_3$-Modified PAA:

To a 250 mL round bottom flask, solid PAA (2.0 g, Mw=450,000 Dalton) and liquid DMSO (100 g) were added. The flask was magnetically stirred until PAA completely dissolved. Solid 4-(dimethylamino)pyridine (DMAP, 0.34 g) and crude liquid 3-azidopropanol (12.5 g) were added to the reaction flask. The reaction mixture was stirred until all DMAP was completely dissolved, then solid N-(3-Dimethylaminopropyl)-N'-ethylcarbodiimide hydrochloride (EDC, 2.67 g) was added. The reaction mixture was stirred at room temperature for 16 h. After 16 hours, the mixture was added dropwise into a 1 L beaker containing 900 mL deionized water, yielding a precipitate. The supernatant was discarded, and the precipitate was washed twice with deionized water (500 mL each). The precipitate was redissolved in deionized water (400 mL) with the aid of 0.1N NaOH, and yielded a transparent solution with solids content of 0.78 wt % and pH of 9.70.

Synthesis of Alkyne-Modified PAA:

To a 250 mL round bottom flask, solid PAA (2.0 g, Mw=450,000 Dalton) and liquid DMSO (100 g) were added. The flask was magnetically stirred until PAA completely dissolved. Solid 4-(dimethylamino)pyridine (DMAP, 0.34 g) and liquid propargyl alcohol (9.34 g) were added to the reaction flask. The reaction mixture was stirred until all DMAP was completely dissolved, then solid N-(3-Dimethylaminopropyl)-N'-ethylcarbodiimide hydrochloride (EDC, 2.67 g) was added. The reaction mixture was stirred at room temperature for 16 hours. After 16 hours, the mixture was added dropwise into a 1 L beaker containing 900 mL deionized water, yielding a precipitate. The supernatant was discarded, and the precipitate was washed twice with deionized water (500 mL each). The precipitate was redissolved in deionized water (600 mL) with the aid of 0.1N NaOH, and yielded a transparent solution with solids content of 0.50 wt % and pH of 9.75.

Preparation of Polymer Particle from a Mixture of $N_3$-Modified PAA/Alkyne-Modified PAA and Crosslinking Reaction Using CuSO4/Sodium Ascorbate as the Catalyst:

To a 250 mL beaker equipped with a stir bar, $N_3$-modified PAA aqueous solution (12.85 g of 0.78 wt %), alkyne-modified PAA aqueous solution (20.04 g of 0.50 wt %) and deionized water (167.11 g) were weighed. The result mixture contained 0.1 wt % of polymers with a pH value of 8.03 and a viscosity of 359 second. 50 mL of the mixture was transferred to a 100 mL beaker equipped with a stir bar. While stirring and monitoring the pH by a pH meter, aqueous HCl (1N) was added dropwise to the beaker. The transparent solution became translucent at around pH 6.2 and then opaque at around 5.7. Acidifying was stopped; viscosity of the dispersion and particle size were measured. DLS measurement determined the average particle size was 128 nm (100% volume intensity), and the viscosity was 68 second at 22° C.

The opaque mixture (25 g) was transferred to a 50 mL beaker along with a stir bar. Freshly prepared $CuSO_4$ (0.050 g of 0.063 M), and sodium ascorbate (0.050 g of 0.16 M) were added to the mixture. The reaction mixture was stirred for 16 hours at room temperature. DLS measurements of the reacted mixture showed the average particle size was 142 nm (100% volume intensity). Increasing the pH of the dispersion to 10, the opaque mixture remained opaque, while the average particle size increased to 222 nm (100% volume intensity). Unlike the sample not treated with $CuSO_4$/sodium ascorbate, the opaque mixture became transparent as the pH of the dispersion increased above 6.5. The results indicate that the presence of $CuSO_4$/sodium ascorbate reagents catalyzed the crosslinking reaction between the azide and alkyne groups, and thus locked in polymer particle structure.

D. Formulation of Polymer Nanoparticles Associated with Active Ingredients:

Example 6: Loading Picloram Using Polymer Particles 2.5 mL methanol, 8.9 mg polymer particles prepared according to Example 3, and 20.64 mg Picloram (4-amino-3,5,6-trichloro-2-pyridinecarboxylic acid) were mixed in a 10 mL glass vial. The pH of the solution was maintained at 2 by adding 2 N HCl solution. The above solution was vortexed until it became transparent. The methanol was removed by evaporation. 2 mL DI water was added to dried mixture, and pH of the solution was maintained at 8 by adding 0.5 N NaOH solution. The solution was vortexed until it was transparent. This solution was freeze-dried to obtain dry powder of polymer particles loaded with Picloram. The amount of Picloram retained in each step was measured using UV-Vis spectroscopy.

Example 7: Loading Imazethapyr Using Polymer Particles 1 mL methanol, 6.8 mg polymer particles prepared according to Example 3, and 10 mg Imazethapyr (2-[4,5-dihydro-4-methyl-4-(1-methylethyl)-5-oxo-1H-imidazol-2-yl]-5-ethyl-3-pyridinecarboxylic acid) were mixed in a 5 mL glass vial. The pH of the solution was maintained at 2 by adding 2 N HCl solution. The above solution was vortexed until it became transparent. The methanol was removed by evaporation. 1 mL DI water was added to dried mixture, and pH of the solution was maintained at 8 by adding 0.5 N NaOH solution. The solution was vortexed until it was transparent. This solution was freeze-dried to obtain dry powder of polymer particles loaded with Imazethapyr. The amount of Imazethapyr retained in each step was measured using UV-Vis spectroscopy.

Example 8: Loading Thifensulfuron-Methyl Using Polymer Particles 8 mL methanol, 2.1 mg polymer particles prepared according to Example 3, and 18.2 mg Thifensulfuron-methyl (methyl 3-[[[[(4-methoxy-6-methyl-1,3,5-triazin-2-yl)amino]carbonyl]amino]sulfonyl]-2-thiophenecarboxylate) were mixed in a 10 mL glass vial. The pH of the solution was maintained at 2 by adding 2 N HCl solution. The above solution was vortexed until it became transparent. The methanol was removed by evaporation. 1 mL DI water was added to dried mixture, and pH of the solution was maintained at 8 by adding 0.5 N NaOH solution. The solution was vortexed until it was transparent. This solution was freeze-dried to obtain dry powder of polymer particles loaded with Thifensulfuron-methyl. The amount of Thifensulfuron-methyl retained in each step was measured using UV-Vis spectroscopy.

Example 9: Loading Thiamethoxam Using Polymer Particles 4 mL methanol, 3.1 mg polymer particles prepared according to Example 3, and 28.5 mg Thiamethoxam were mixed in a 10 mL glass vial. The pH of the solution was maintained at 2 by adding 2 N HCl solution. The above solution was vortexed until it became transparent. The methanol was removed by evaporation. 1 mL DI water was added to dried mixture, and pH of the solution was maintained at 8 by adding 0.5 N NaOH solution. The solution was vortexed until it was transparent. This solution was freeze-dried to obtain dry powder of polymer particles loaded with Thiamethoxam. The amount of Thiamethoxam retained in each step was measured using UV-Vis spectroscopy.

Example 10: Loading Thiamethoxam Using Polymer Particles 4 mL methanol, 3.1 mg polymer particles prepared according to Example 1, and 28.5 mg Thiamethoxam (3-[(2-chloro-5-thiazolyl)methyl]tetrahydro-5-methyl-N-nitro-4H-1,3,5-oxadiazin-4-imine) were mixed in a 10 mL glass vial. The pH of the solution was maintained at 2 by adding 2 N HCl solution. The above solution was vortexed until it became transparent. The methanol was removed by evaporation. 1 mL DI water was added to dried mixture, and pH of the solution was maintained at 8 by adding 0.5 N NaOH solution. The solution was vortexed until it was transparent. This solution was freeze-dried to obtain dry powder of polymer particles loaded with Thiamethoxam. The amount of Thiamethoxam retained in each step was measured using UV-Vis spectroscopy.

Example 11: Loading Thiamethoxam Using HEMA-Modified PAA (NaCl and UV Treated)

4 mL methanol, 3.2 mg HEMA-modified PAA prepared according to Example 4, and 28.4 mg Thiamethoxam (3-

[(2-chloro-5-thiazolyl)methyl]tetrahydro-5-methyl-N-nitro-4H-1,3,5-oxadiazin-4-imine) were mixed in a 10 mL glass vial. The HEMA-modified PAA was treated with UV radiation in the presence of NaCl. The pH of the solution was maintained at 2 by adding 2 N HCl solution. The above solution was vortexed until it became transparent. The methanol was removed by evaporation. 2 mL DI water was added to dried mixture, and pH of the solution was maintained at 8 by adding 0.5 N NaOH solution. The solution was vortexed until it was transparent. This solution was freeze-dried to obtain dry powder of HEMA-modified PAA loaded with Thiamethoxam. The amount of Thiamethoxam retained in each step was measured using UV-Vis spectroscopy.

Example 12: Slow Release of Thiamethoxam ("TMX") from Polymer Nanoparticles 10 mg of solid nanocapsule formulation prepared from Example 9, and 20 mL DI water were added to a 50 ml glass vial (with a sealing cape). Slow release testing was timed upon addition of DI water. The above solution was then continuously pumped through a Minimate Tangential Flow Filtration capsule (TFF, 3K, Omega membrane, PALL). The testing device is shown in the FIG. 8A below. Samples from the release medium were collected from permeate at 0.2 ml at the required time intervals, the rest of permeate was returned back to the glass vial immediately.

All the samples taken were diluted by DI water to appropriate concentration of TMX, and then analyzed by UV-vis to quantify its concentration of TMX from a calibration curve of TMX in water. The slow release rate at specific testing time was calculated based on the quantification of TMX in the samples taken during the test, which was demonstrated by plotting the % release as function of the respective time point. The typical slow release characteristics was shown in the FIG. 8B.

Example 13: Loading Atrazine Using HEMA-Modified PAA Particles

50 µL ethyl acetate, 1.2 mg polymer particles prepared according to Example 2, and 1 mL DI water were mixed in a 5 mL glass vial. The pH of the solution was measured at 3. The above solution was stirred until oil phase disappeared. Then 120 µL ethyl acetate solution of Atrazine (6-chloro-N-ethyl-N'-(1-methylethyl)-1,3,5-triazine-2,4-diamine, Atrazine concentration in solution: 22 mg/mL) was added and stirred until oil phase disappeared. The ethyl acetate was removed by evaporation to form a suspension. This solution was freeze-dried to obtain dry powder of polymer particles loaded with Atrazine. The amount of Atrazine retained in each step was measured using UV-Vis spectroscopy.

Example 14: Loading Thiamethoxam Using HEMA-Modified PAA Particles

100 µL ethyl acetate, 1.2 mg polymer particles prepared according to Example 2, and 1 mL DI water were mixed in a 5 mL glass vial. The pH of the solution was measured at 3. The above solution was stirred until oil phase disappeared. Then 6.5 mg Thiamethoxam (TMX, 95%) was added and stirred until TMX disappeared. The ethyl acetate was removed by evaporation to form a suspension. This solution was freeze-dried to obtain dry powder of polymer particles loaded with TMX. The amount of TMX retained in each step was measured using UV-Vis spectroscopy.

Example 15: Loading Azoxystrobin Using HEMA-Modified PAA Particles 11.32 mg polymer particles prepared according to Example 2, 5.9 mg Azoxystrobin (methyl (αE)-2-[[6-(2-cyanophenoxy)-4-pyrimidinyl]oxy]-α-(methoxymethylene)benzeneacetate) and 4 mL Methanol were mixed in a 10 mL glass vial. The pH of the solution was 3. 8.15 g water was slowly added (0.119 mL/min) under stirring condition. The methanol was removed by evaporation to form a suspension. This solution was freeze-dried to obtain dry powder of polymer particles loaded with Azoxystrobin. The amount of Azoxystrobin retained in each step was measured using UV-Vis spectroscopy.

Example 16: Loading Azoxystrobin Using PAA Particles 3 mL methanol, 11.0 mg polymer particles prepared according to Example 3, and 5.3 mg Azoxystrobin were mixed in a 10 mL glass vial. The above solution was vortexed until it became transparent. The methanol was removed by evaporation. 5 mL DI water was added to dried mixture, and pH of the solution was adjusted to 7 by adding 0.5 N NaOH solution. The solution was stirred to form a suspension. This solution was freeze-dried to obtain dry powder of polymer particles loaded with Azoxystrobin. The amount of Azoxystrobin retained in each step was measured using UV-Vis spectroscopy.

Example 17: Loading Azoxystrobine Using PAA Particles 12.8 mg polymer particles prepared according to Example 3, 6.0 mg Azoxystrobin and 4 mL Methanol were mixed in a 10 mL glass vial. The pH of the solution was measured at 3. 6.0 g water was slowly added (0.119 mL/min) under stirring condition. The methanol was removed by evaporation to form a suspension. This solution was freeze-dried to obtain dry powder of polymer particles loaded with Azoxystrobin. The amount of Azoxystrobin retained in each step was measured using UV-Vis spectroscopy.

E. Polyelectrolytes Collapsed with Active Ingredients:

Example 18: Production of Nanoparticles of 2,4-Dichlorophenoxyacetic Acid (2,4-D) Coated with Cationic Poly(Allylamine)

Solid 2,4-dichlorophenoxyacetic acid (2,4-D) (0.158 g, 0.72 mmol) and fresh deionized water (50 mL) were added to a 100 mL glass beaker, along with a stir bar. The medium was connected to a pH meter and the reading was at 2.76. To the stirring dispersion, aqueous NaOH (10N) was added dropwise. As the pH increased, more solid 2,4-D dissolved the dispersion became more transparent. Eventually, all of the solid 2,4-D dissolved completely, and the solution appeared transparent. The pH and viscosity of the solution was measured at 10.76 and 0.93 cP at 25.4° C. For the reference, the viscosity of pure water was measured using the same instrument and shown a value of 0.92 cP at 26.4° C.

In a different beaker (250 mL) equipped with a magnetic stir bar, solid poly(allylamine) (PAH, $M_w$=70,000) (0.5 g, 5.5 mmol) and 50 mL of deionized water were added, yielding aqueous PAH solution of 1 wt %. The solution appeared clear with pH value of 3.47 and viscosity of 3.00 cP at 26.0° C. Then, the aqueous 2,4-D solution was fed to the stirring PAH solution via a feeding pump, producing nanoparticles of active ingredient coated with PAH. It took about 15 minutes to complete the addition. The nanoparticle dispersion appeared light yellow transparent. The pH and viscosity of the dispersion were measured and shown to have a value of 4.79 and 1.69 cP at 25.1° C. Note that the final concentration of PAH in the nanoparticle dispersion is half of the original solution. For comparison, the viscosity of PAH at this concentration was prepared, measured and obtained with a value of 2.25 cP at 24.6° C., a value that is higher than that of the collapsed nanoparticles (1.69 cP at 25.1° C.). The result of the viscosity measurements indicated that PAH polymers collapsed from the extended configuration when charged 2,4-D was added. In addition, dynamic light scattering (DLS) analyzed by volume intensity distribution showed the mean diameter of the collapsed particles was about 7 nm.

Example 19: Production of Nanoparticles of 2,4-Dichlorophenoxy Acetic Acid (2,4-D) Coated with Cationic Poly(Diallydimethylammonium Chloride) (PDDA)

Solid 2,4-dichlorophenoxyacetic acid (2,4-D) (16.0 g, 72.4 mmol) was ground to fine powder before being transferred to a 2 L glass beaker. Fresh deionized water (1 L) was measured by a 1 L graduate cylinder and transferred to the beaker, along with a stir bar. The medium was connected to a pH meter and the reading was at 2.60. To the stirring dispersion, 10N of aqueous NaOH was added dropwise. As the pH increased, more solid 2,4-D dissolved the dispersion became more transparent. Eventually, all of the solid 2,4-D dissolved completely (about 7 mL of 10N NaOH was added), and the solution appeared transparent. The pH of the solution was 7.44.

In a different beaker (4 L) equipped with a mechanical stirrer, cationic poly(diallydimethylammonium chloride) (PDDA) (146.3 g of 20 wt % PDDA (29.26 g solids PDDA, 181.0 mmol) and 854 mL of deionized water were transferred. The solution appeared transparent. The pH was measured at 4.74. The aqueous 2,4-D solution was fed to the stirring PDDA solution via a feeding pump. It took about 3.5 hrs to complete the addition. The mixture appeared transparent and contained 8.0 g/L of active ingredient (2,4-D). The pH was measured at 6.35 and the viscosity was at 6.75 cP at 26.0° C. Note that the final concentration of PDDA in the nanoparticle dispersion is half of the original solution. For comparison, the viscosity of PDDA this concentration was prepared, measured and obtained with a value of 9.32 cP at 25.3° C., a value that is higher than that of the collapsed nanoparticles (6.75 cP at 26.0° C.). The result of viscosity measurements suggested that PDDA polymers collapsed from the extended configuration when charged 2,4-D was added. In addition, dynamic light scattering (DLS) analyzed by volume intensity distribution showed the mean diameter of the collapsed particles was about 7 nm.

Example 20: Production of Nanoparticles of 2,4-Dichlorophenoxy Acetic Acid (2,4-D) Coated with Cationic Low Molecular Weight Chitosan Polymer Solid 2,4-dichlorophenoxyacetic acid (2,4-D) (18.0 g, 81.4 mmol) was ground to fine powder before transferred to a 2 L glass beaker. Fresh deionized water (1062 mL) was measured by a 1 L graduate cylinder and transferred to the beaker, along with a stir bar. The medium was connected to a pH meter and the pH was 2.56. To the stirring dispersion, 10N of aqueous NaOH was added dropwise. As the pH increased, more solid 2,4-D dissolved the dispersion became more transparent. Eventually, all of the solid 2,4-D dissolved completely (about 8 mL of 10N NaOH was added), and the solution appeared transparent. The pH of the solution was measured at 7.60.

In a different beaker (4 L) equipped with a mechanical stirrer, solid chitosan (low molecular weight, 32.9 g, 204 mmol) and 1062 mL of deionized water were transferred. The solution appeared light yellow with low viscosity due to incompletely dissolved chitosan. Liquid acetic acid (11.0 g, 183 mmol) was added dropwise to the chitosan dispersion. The viscosity of the dispersion increased drastically as the acetic acid was added. The dispersion was kept stirring for about 1 hour until all solid chitosan was completely dissolved. Then, the aqueous 2,4-D solution was fed to the stirring chitosan solution via a feeding pump. During the addition, the solution began to foam. The addition of 2,4D solution was completed in about 3.5 hours. The mixture appeared light yellow transparent. The solution remained at room temperature overnight so allow the foam to migrated to the surface. The next days, foams were removed. The pH and viscosity were 5.16 and 17.4 cP at 23.4° C., respectively. For comparison, the viscosity of low molecular weight chitosan alone at this concentration was 23.3 cP at 24.0° C., a value that is higher than that of the collapsed nanoparticles (17.4 cP at 23.4° C.). The result of the viscosity measurement indicates that the chitosan polymers collapsed from their extended configuration when 2,4-D was added. Dynamic light scattering (DLS) analyzed by volume intensity distribution showed the mean diameter of the collapsed particles to be about 4 nm.

Example 21: Plant Treatment Using Active Ingredient Associated with Polymer Nanoparticles Aqueous polymer nanoparticles containing 2,4-D prepared in Example 20 were directly used for plant treatment. The 2,4-D concentration in this formulation is 8 g/L. Two active concentrations (8 g/L and 4 g/L) were used for testing on plants. Plants were grown in trays for 2 weeks prior to treatment and organized in a randomized block design during the treatment. One tray consisted of 6 plants (barley, barnyard grass, lambsquarters, red-root pigweed, low cudweed and field mint), which represent various crop and weed species. The treatment was applied by misting plants with a mist bottle, calibrated by apply the spay solution at a rate equivalent to 200 liters per hectare. Visual phytotoxicity (% plant damage) rating was taken at 4, 8, 12 and 15 days after treatment. Ratings were entered into a statistical software program and analysis of variance was run on the data. Mean separation was performed when analysis of variance suggested significant differences between treatments.

Two aqueous solutions containing the same amount (8 g/L and 4 g/L) of 2,4-D prepared without chitosan polymers was used as the controls for comparison.

The result shows that the formulation containing nanoparticles of chitosan collapsed by 2,4-D provided slightly increased levels of plant damage as compared to the control.

Example 22: Production of Nanoparticles of 2,4-Dichlorophenoxy Acetic Acid (2,4-D) Coated with Cationic High Molecular Weight Chitosan Polymer Solid 2,4-dichlorophenoxyacetic acid (2,4-D) (8.0 g, 36.2 mmol) was ground to a fine powder before it was transferred to a 2 L glass beaker. Fresh deionized water (1 L) was measured by a 1 L graduate cylinder and transferred to the beaker, along with a stir bar. The medium was connected to a pH meter and the reading was 2.76. To the stirring dispersion, 10N of aqueous NaOH was added dropwise. As the pH increased, more of the solid 2,4-D dissolved and the dispersion became more transparent. Eventually, all solid 2,4-D dissolved completely, and the solution appeared transparent. The pH of the solution was 8.50.

In a different beaker (4 L) equipped with a mechanical stirrer, solid chitosan (high molecular weight, 14.6 g, 90.5 mmol) and 1 L of deionized water were added. The solution appeared light yellow with low viscosity due to incompletely dissolved chitosan. Liquid acetic acid (4.89 g, 81.4 mmol) was added dropwise to the chitosan dispersion. The viscosity of the dispersion increased drastically as the acetic acid was added. The dispersion was kept stirring for about 2 hours until all solid chitosan was completely dissolved. Then, the aqueous 2,4-D solution was fed to the stirring chitosan solution via a feeding pump. During the addition, the solution began to foam. The addition of 2,4D solution was completed in about 3.5 hours. The mixture appeared light yellow transparent. The solution remained at room temperature overnight so allow the foam to migrated to the surface. The next day, the foam were removed. The pH and viscosity were 5.16 and 46.3 cP at 23.3° C., respectively. For comparison, the viscosity of high molecular weight chitosan alone at this concentration was 64.3 cP at 23.4° C., a value higher than that of the collapsed nanoparticles (46.3 cP at 23.3° C.). The viscosity measurements suggest that chitosan polymers collapsed from their extended configuration when charged 2,4-D was added. In addition, dynamic light scattering analyzed by volume intensity distribution showed the mean diameter of the collapsed particles was about 4 nm.

Example 23: Production of Nanoparticles of Glyphosate Coated with Cationic PDDA Solid glyphosate (N-(phosphonomethyl)glycine) (8.0 g, 94.6 mmol), and fresh deionized water (1 L) were added to a 2 L beaker along with a stir bar. The medium was connected to a pH meter and the reading was 2.20. To the stirring dispersion, aqueous NaOH (50 wt %) was added dropwise. As the pH increased to 3, all of the solid glyphosate completely dissolved, and the dispersion became clear. Aqueous NaOH (50 wt %) was added until the pH of the medium reached 7.2.

In a different beaker (4 L) equipped with a mechanical stirrer, cationic poly(diallydimethylammonium chloride) (PDDA) (191 g of 20 wt % PDDA in water, 237 mmol) and 819 mL of deionized water were transferred. The solution appeared transparent. The pH was 4.74. The aqueous glyphosate solution was fed to the stirring PDDA solution via a feeding pump. The addition of 2,4D solution was completed in about 3.5 hours. The mixture appeared transparent and contained 4.0 g/L of active ingredient (glyphosate) with a pH of 6.75 and a viscosity of 7.42 cP at 24.0° C. In addition, dynamic light scattering (DLS) analyzed by volume intensity showed 2 distributions with the mean diameters of the collapsed particles at 2 nm (67%) and 8 nm (33%).

F. Synthesis of Surface-Active Agent of Active Ingredients, their Formulations, and their Uses in the Increase Loading of Active Ingredients in Nanoparticles Collapsed by Active Ingredients:

Example 24: Esterification of 2,4-D with Carbowax MPEG 350 (Supplied from Dow, Methoxy-Terminated Poly(Ethylene Glycol), Mn=350) Using Toluene as the Solvent, Concentrated $H_2SO_4$ as the Catalyst Solid 2,4-D (3.0 g, 13.6 mmol), liquid Carbowax MPEG 350 (5.0 g, 14.3 mmol), toluene (150 mL) were added to a 250 mL round bottom flask along with a stir bar. The reaction flask was connected to a Dean-Stark trap and a condenser. The reaction mixture was refluxed for 24 hours and then cooled to room temperature. Thin layer chromatography using a mixture of ethyl acetate and toluene (50/50, v/v) as the mobile solvent was used to check for the completion of the reaction. Toluene was removed by rotary evaporator, yielded a slight yellow liquid of surface-active agent of the 2,4-D active ingredient. Residual toluene was further removed by a vacuum pump. $^1$H-NMR (300 MHz, $D_2O$): δ 3.38 (s, 3H, $\underline{H_3}$—$(OCH_2CH_2)_n$—$OCH_2CH_2$—O(O)C—), 3.36-3.73 (m, PEG, —($CH_3$—$(OC\underline{H_2}C\underline{H_2})_n$—$OC\underline{H_2}CH_2$—O(O)C—), 4.36 (t, 2H, $CH_3$—$(OCH_2CH_2)_n$—$OCH_2C\underline{H_2}$—O(O)C—), 6.81 (d, 1H, aromatic-H), 7.18 (dd, 1H, aromatic-H), 7.38 (d, 1H, aromatic H).

Example 25: Esterification of 2,4-D with Carbowax MPEG 750 (Supplied from Dow, Methoxy-Terminated Poly(Ethylene Glycol), Actual Mn=756) Using Silica Gel as the Catalyst in the Absence of an Organic Solvent at 150° C.

Solid 2,4-D (20.0 g, 90.5 mmol), liquid Carbowax MPEG 750 (68.4 g, 90.5 mmol), silica gel 60 Å (200-400 mesh) (1.0 g) were added to a 250 mL round bottom flask along with a stir bar. The reaction flask was connected to a Dean-Stark trap and a condenser. The reaction mixture was heated to 150° C. under a gentle stream of nitrogen gas. During the reaction, the side product of the esterification reaction, water, was condensed and collected in the Dean-Stark trap. Thin layer chromatography was used to monitor the completion of the reaction. The reaction was complete in 3 hours. The crude product was filtered to remove silica gel, and yielded a slight yellow liquid of surface-active agent of the 2,4-D active ingredient. $^1$H-NMR (300 MHz, $D_2O$): δ 3.38 (s, 3H, $C\underline{H_3}$—$(OCH_2CH_2)_n$—$OCH_2CH_2$—O(O)C—), 3.36-3.73 (m, PEG, —($CH_3$—$(OC\underline{H_2}C\underline{H_2})_n$—$OC\underline{H_2}CH_2$—O(O)C—), 4.36 (t, 2H, $CH_3$—$(OCH_2CH_2)_n$—$OCH_2C\underline{H_2}$—O(O)C—), 6.81 (d, 1H, aromatic-H), 7.18 (dd, 1H, aromatic-H), 7.38 (d, 1H, aromatic H).

Example 26: Formulation of Surface-Active Agent of 2,4-D

Liquid 2,4-D surfactant produced according to Example 24 (34.72 g, equivalent to 4.0 g of 2,4-D itself) and 2 L deionized water were transferred to a 3 L plastic beaker along with a stir bar. The 2,4-D surfactant was completely dissolved, and the solution appeared slightly yellow but transparent with a pH value of 2.76. A few drops of aqueous NaOH (10N) were added to the solution to increase the pH to 6.65. At this pH, the viscosity of the solution was 1.08 cP at 24.0° C., and dynamic light scattering result obtained by volume distribution analysis showed a single distribution with the mean diameter of 252 nm.

G. Combinations of Surface-Active Agents of Active Ingredients and Polymer-Encapsulated Nanoparticles of Active Ingredients Example 27: Production of Nanoparticles Containing an Increased Loading of 2,4-D Solid 2,4-dichlorophenoxyacetic acid (2,4-D) (4.0 g, 18.1 mmol) was ground to a fine powder before transferred to a 2 L glass beaker. Fresh deionized water (1 L) was measured by a 1 L graduate cylinder and transferred to the beaker, along with a stir bar. The medium was connected to a pH meter. To the stirring dispersion, aqueous NaOH (10N) was added dropwise. As the pH increased, more solid 2,4-D dissolved the dispersion became more transparent. Eventually, all solid 2,4-D dissolved completely, and the solution appeared transparent. The pH of the solution was measured at 9.20.

In a different beaker (4 L) equipped with a mechanical stirrer, cationic poly(diallydimethylammonium chloride) (PDDA) (36.57 g of 20 wt % PDDA in water, 45.2 mmol) and 900 mL of deionized water were transferred. The solution appeared transparent. The aqueous 2,4-D solution was fed to the stirring PDDA solution via a feeding pump. The addition of 2,4D solution was completed in about 3.5 hours. The mixture appeared transparent and contained 2.0 g/L of active ingredient (2,4-D). The pH and viscosity of the nanoparticle dispersion were 7.06 and 3.18 cP at 24.1° C., respectively. Dynamic light scattering (DLS) analyzed by volume intensity distribution showed the mean diameter of the collapsed particles was about 3 nm. In a 250 mL beaker equipped with a stir bar, liquid of surface-active agent of active ingredient (prepared according to example 24) (17.35 g) and deionized water (64 mL) were transferred. The mixture was stirred until the surface-active agent of active ingredient completely dissolved. The pH of the surface-active agent of active ingredient was measured and showed a value of 2.64. Aqueous NaOH (10N) was used to increase the pH of the surface-active agent of active ingredient to 5.98. Then the surface-active agent of active ingredient solution was added dropwise to the dispersion of nanoparticles of active ingredient encapsulated by PDDA. The result mixture appeared transparent with light yellow color and has a pH value of 6.23 and the viscosity of 2.51 cP at 23.1° C. DLS result of this polymer solution was shown a single distribution with a mean diameter of 4 nm.

N. Soil Mobility

This example demonstrates that PAA capsules can be loaded with active ingredient and moved through Ottawa sand. A hydrophobic fluorescent dye (modified Hostasol Yellow) was used as a model active ingredient.

Example 28

Standard Ottawa sand (VWR, CAS#14808-60-7) was washed twice with deionized water and dried in air prior to use. The dried sand was used as an immobile phase in the column and to load dyes, with and without PAA capsules, onto columns.

Preparation Samples with and without PAA Capsules:

In a 20 mL vial, modified Hostasol Yellow dye (0.0035 g), dried Ottawa sand (2.0 g) and methanol (10 g) were weighed. The mixture was stirred until all dyes were completely dissolved. Methanol was completely removed by rotary evaporator. This process allowed the dyes to be adsorbed onto sand particles.

In a different 20 mL vial, modified Hostasol Yellow dye (0.0035 g), PAA capsules (0.010 g) prepared according to Example 1 and methanol (10 g) were weighed. The mixture was stirred until all dyes were completely dissolved. Methanol was partially removed by rotary evaporator. Dried sand (2.0 g) was added to the solution and then the methanol was removed completely.

Preparation Columns:

Two glass pipettes were used as columns. Dried sand (1.8 g) was loaded into each column to a height of 2 in. Each column was washed with 10 mL deionized water. The eluted water was collected for UV analysis. Two dried samples (0.5 g each) were loaded onto the columns and eluted with deionized water (10 g). The eluent from the sample containing PAA capsules appeared yellow whereas the eluent from the sample without the capsules appeared clear. In addition, the column contained the sample without the PAA capsules was eluted with an aqueous PAA capsule dispersion (10 g deionized water, 0.010 g PAA capsules). The eluent from this experiment appeared clear. This result indicates that modified Hostasol Yellow was not transferred from the column to the capsules.

Figure 9:
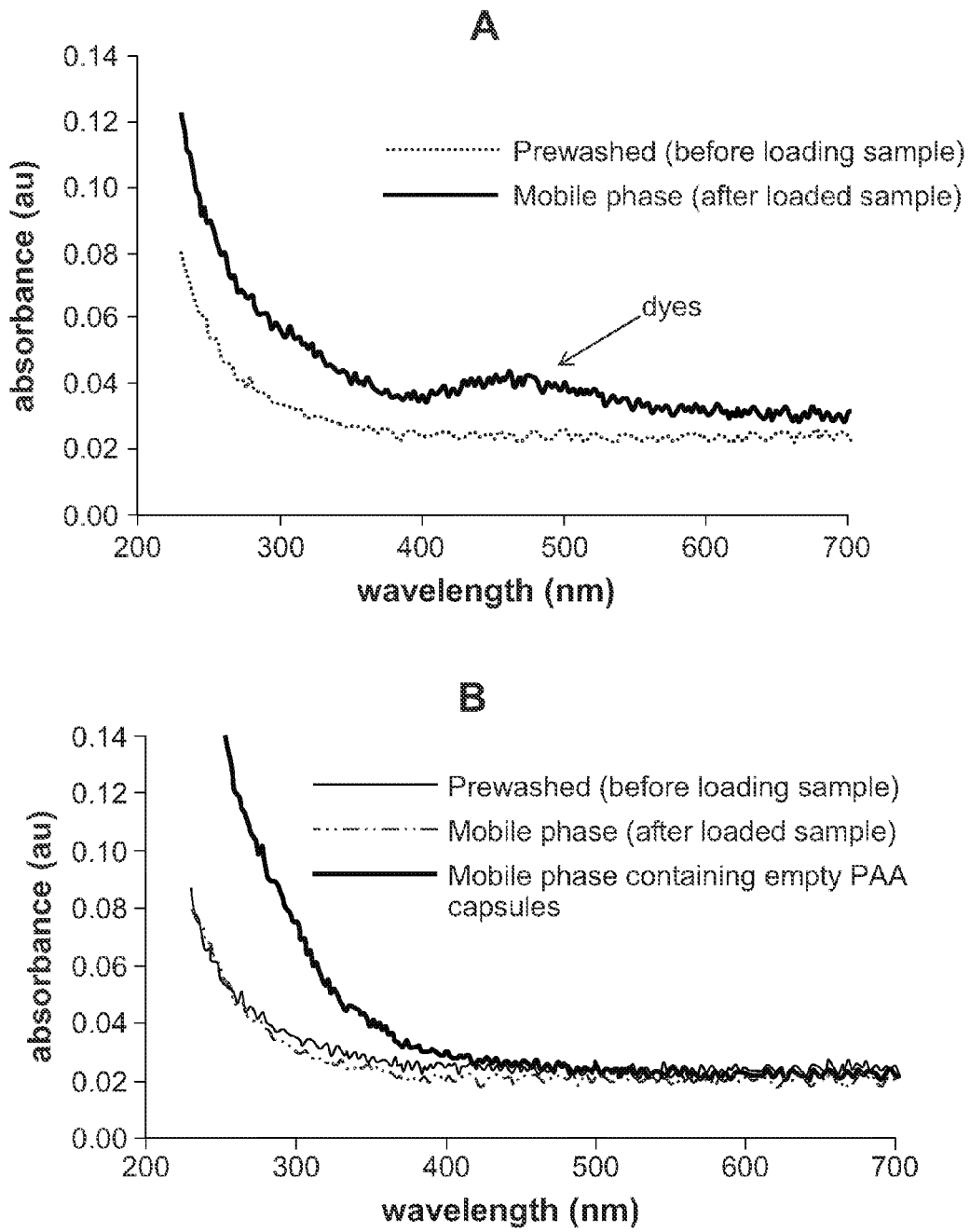
FIG. 9 shows exemplary soil mobility of Hostasol Yellow loaded polymer nanoparticles. A: UV-vis spectra of the eluent for Hostasol Yellow loaded hollow polymer nanoparticles. B: UV spectra of the eluent for Hostasol Yellow without the hollow polymer nanoparticles.

FIG. 9A: UV spectrum of A) The eluents collected from the column containing the sample loaded with PAA capsules. The modified Hostasol Yellow showed an absorption peak maximized at 480 nm, 9B) The eluents collected from the column containing the sample loaded without PAA capsules. Note that in this column, it was flushed after the elution test with an aqueous dispersion containing empty PAA capsules.

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION BY REFERENCE

All publications and patent documents cited in this application are incorporated by reference in their entirety for all purposes to the same extent as if the contents of each individual publication or patent document were incorporated herein.

What is claimed is:

1. A composition comprising a polymer nanoparticle and at least one organic, neutral, non-ionic agricultural active compound associated with the polymer nanoparticle; wherein:
   the polymer nanoparticle is less than 100 nm in diameter and cross-linked;
   the polymer nanoparticle comprises a collapsed, water-soluble polyelectrolyte having a molecular weight of at least about 100,000 Dalton; and
   the at least one organic, neutral, non-ionic, agricultural active compound is a nicotinic acetylcholine receptor agonist insecticide.

2. The composition of claim 1, wherein the nicotinic acetylcholine receptor agonist insecticide is selected from the group consisting of imidacloprid, thiamethoxam, acetamiprid, and combinations thereof.

3. The composition of claim 1, wherein the polymer nanoparticle is less than 50 nm in diameter.

4. The composition of claim 1, wherein the polymer nanoparticle comprises multiple collapsed, water-soluble polyelectrolyte molecules, each having a molecular weight of at least about 100,000 Dalton.

5. A dispersion comprising the composition of claim 1, wherein the at least one organic, neutral, non-ionic agricultural active compound is dispersed at a concentration higher than its solubility in the absence of the polymer nanoparticle.

6. The composition of claim 1, wherein the collapsed, water-soluble polyelectrolyte is poly(acrylic acid), poly(methacrylic acid), poly(styrene sulfonate), chitosan, poly(dimethyldiallylammonium chloride), poly(allylamine hydrochloride), copolymers or graft polymers thereof, or combinations thereof.

7. The composition of claim 1, wherein at least a portion of the at least one organic, neutral, non-ionic agricultural active compound is in the interior of the polymer nanoparticle.

8. The composition of claim 1, wherein at least a portion of the at least one organic, neutral, non-ionic agricultural active compound is on the surface of the polymer nanoparticle.

9. The composition of claim 1, wherein the at least one organic, neutral, non-ionic agricultural active compound remains associated with the polymer nanoparticle after being exposed to a solvent.

10. The composition of claim 1, wherein the composition is an extended or sustained release composition.

11. The composition of claim 1, wherein the composition is a triggered release composition.

12. The composition of claim 1, wherein the polymer nanoparticle has a cavity.

13. The composition of claim 1, wherein the polymer nanoparticle has a network structure.

14. The composition of claim 1, wherein the at least one organic, neutral, non-ionic agricultural active compound associated with the polymer nanoparticle has different mobility in soil than it has when not associated with the polymer nanoparticle.

15. The composition of claim 1, wherein the collapsed, water-soluble polyelectrolyte has a molecular weight of at least about 250,000 Daltons.

* * * * *